United States Patent
Tanner et al.

(10) Patent No.: US 12,102,813 B2
(45) Date of Patent: Oct. 1, 2024

(54) MOTOR ASSEMBLY FOR CATHETER PUMP

(71) Applicant: TC1 LLC, St. Paul, MN (US)

(72) Inventors: Adam R. Tanner, Mountain View, CA (US); Richard L. Keenan, Livermore, CA (US); Doug M. Messner, Livermore, CA (US); Michael R. Butler, Dublin, CA (US)

(73) Assignee: TC1 LLC, St. Paul, MN (US)

( * ) Notice: Subject to any disclaimer, the term of this patent is extended or adjusted under 35 U.S.C. 154(b) by 853 days.

(21) Appl. No.: 17/112,791

(22) Filed: Dec. 4, 2020

(65) Prior Publication Data
US 2021/0085847 A1   Mar. 25, 2021

Related U.S. Application Data

(63) Continuation of application No. 16/742,129, filed on Jan. 14, 2020, now Pat. No. 11,219,756, which is a
(Continued)

(51) Int. Cl.
*A61M 60/419* (2021.01)
*A61M 60/13* (2021.01)
(Continued)

(52) U.S. Cl.
CPC .......... *A61M 60/419* (2021.01); *A61M 60/13* (2021.01); *A61M 60/216* (2021.01);
(Continued)

(58) Field of Classification Search
CPC ............................................. A61M 60/00–90
See application file for complete search history.

(56) References Cited

U.S. PATENT DOCUMENTS

| 1,902,418 A | 3/1933 | Pilgrim |
| 2,356,659 A | 8/1944 | Aguiar |
| (Continued) | | |

FOREIGN PATENT DOCUMENTS

| CA | 2256427 A1 | 10/1998 |
| CA | 2322012 A1 | 9/1999 |
| (Continued) | | |

OTHER PUBLICATIONS

Siess et al., "Hydraulic refinement of an intraarterial microaxial blood pump", The International Journal of Artificial Organs, 1995, vol. 18, No. 5, pp. 273-285.
(Continued)

*Primary Examiner* — Amanda K Hulbert
*Assistant Examiner* — Philip C Edwards
(74) *Attorney, Agent, or Firm* — Armstrong Teasdale LLP

(57) ABSTRACT

A catheter pump is disclosed herein. The catheter pump can include a catheter assembly that comprises a drive shaft and an impeller coupled to a distal end of the drive shaft. A driven assembly can be coupled to a proximal end of the drive shaft within a driven assembly housing. The catheter pump can also include a drive system that comprises a motor and a drive magnet coupled to an output shaft of the motor. The drive system can include a drive assembly housing having at least one magnet therein. Further, a securement device can be configured to prevent disengagement of the driven assembly housing from the drive assembly housing during operation of the pump.

20 Claims, 18 Drawing Sheets

Related U.S. Application Data continuation of application No. 15/242,024, filed on Aug. 19, 2016, now Pat. No. 10,576,193, which is a continuation of application No. 13/802,468, filed on Mar. 13, 2013, now Pat. No. 9,421,311.

(60) Provisional application No. 61/667,869, filed on Jul. 3, 2012.

(51) Int. Cl.
*A61M 60/148* (2021.01)
*A61M 60/216* (2021.01)
*A61M 60/414* (2021.01)
*A61M 60/422* (2021.01)
*A61M 60/515* (2021.01)
*A61M 60/538* (2021.01)

(52) U.S. Cl.
CPC ........ *A61M 60/422* (2021.01); *A61M 60/515* (2021.01); *A61M 60/538* (2021.01); *A61M 60/148* (2021.01); *A61M 60/414* (2021.01); *Y10T 29/49236* (2015.01)

(56) References Cited

U.S. PATENT DOCUMENTS

| | | |
|---|---|---|
| 2,649,052 A | 8/1953 | Weyer |
| 2,664,050 A | 12/1953 | Abresch |
| 2,684,035 A | 7/1954 | Kemp |
| 2,776,161 A | 1/1957 | Dingman et al. |
| 2,789,511 A | 4/1957 | Doble |
| 2,896,926 A | 7/1959 | Chapman |
| 2,935,068 A | 5/1960 | Donaldson |
| 3,080,824 A | 3/1963 | Boyd et al. |
| 3,135,943 A | 6/1964 | Richard |
| 3,455,540 A | 7/1969 | Marcmann |
| 3,510,229 A | 5/1970 | Smith |
| 3,812,812 A | 5/1974 | Hurwitz |
| 3,860,713 A | 1/1975 | Shema et al. |
| 3,860,968 A | 1/1975 | Shapiro |
| 3,904,901 A | 9/1975 | Renard et al. |
| 3,995,617 A | 12/1976 | Watkins et al. |
| 4,115,040 A | 9/1978 | Knorr |
| 4,129,129 A | 12/1978 | Amrine |
| 4,135,253 A | 1/1979 | Reich et al. |
| 4,143,425 A | 3/1979 | Runge |
| 4,149,535 A | 4/1979 | Volder |
| 4,155,040 A | 5/1979 | Ackerman et al. |
| 4,304,524 A | 12/1981 | Coxon |
| 4,382,199 A | 5/1983 | Isaacson |
| 4,392,836 A | 7/1983 | Sugawara |
| 4,458,366 A | 7/1984 | Macgregor et al. |
| 4,540,402 A | 9/1985 | Aigner |
| 4,560,375 A | 12/1985 | Schulte et al. |
| 4,589,822 A | 5/1986 | Clausen et al. |
| 4,625,712 A | 12/1986 | Wampler |
| 4,655,745 A | 4/1987 | Corbett |
| 4,686,982 A | 8/1987 | Nash |
| 4,696,667 A | 9/1987 | Masch |
| 4,704,121 A | 11/1987 | Moise |
| 4,728,319 A | 3/1988 | Masch |
| 4,753,221 A | 6/1988 | Kensey et al. |
| 4,769,006 A | 9/1988 | Papantonakos |
| 4,817,586 A | 4/1989 | Wampler |
| 4,846,152 A | 7/1989 | Wampler et al. |
| 4,895,557 A | 1/1990 | Moise et al. |
| 4,900,227 A | 2/1990 | Trouplin |
| 4,902,272 A | 2/1990 | Milder et al. |
| 4,906,229 A | 3/1990 | Wampler |
| 4,908,012 A | 3/1990 | Moise et al. |
| 4,919,647 A | 4/1990 | Nash |
| 4,944,722 A | 7/1990 | Carriker et al. |
| 4,955,856 A | 9/1990 | Phillips |
| 4,957,504 A | 9/1990 | Chardack |
| 4,964,864 A | 10/1990 | Summers et al. |
| 4,969,865 A | 11/1990 | Hwang et al. |
| 4,976,270 A | 12/1990 | Parl et al. |
| 4,985,014 A | 1/1991 | Orejola |
| 4,994,017 A | 2/1991 | Yozu |
| 4,995,857 A | 2/1991 | Arnold |
| 5,000,177 A | 3/1991 | Hoffmann et al. |
| 5,021,048 A | 6/1991 | Buckholtz |
| 5,045,072 A | 9/1991 | Castillo et al. |
| 5,049,134 A | 9/1991 | Golding et al. |
| 5,061,256 A | 10/1991 | Wampler |
| 5,089,016 A | 2/1992 | Millner et al. |
| 5,092,844 A | 3/1992 | Schwartz et al. |
| 5,098,256 A | 3/1992 | Smith |
| 5,106,368 A | 4/1992 | Uldall et al. |
| 5,112,200 A | 5/1992 | Isaacson et al. |
| 5,112,292 A | 5/1992 | Hwang et al. |
| 5,112,349 A | 5/1992 | Summers et al. |
| 5,129,883 A | 7/1992 | Black |
| 5,142,155 A | 8/1992 | Mauze et al. |
| 5,145,637 A | 9/1992 | Richardson et al. |
| 5,147,186 A | 9/1992 | Buckholtz |
| 5,163,910 A | 11/1992 | Schwartz et al. |
| 5,169,378 A | 12/1992 | Figuera |
| 5,171,212 A | 12/1992 | Buck et al. |
| 5,190,528 A | 3/1993 | Fonger et al. |
| 5,195,960 A | 3/1993 | Hossain et al. |
| 5,201,679 A | 4/1993 | Velte et al. |
| 5,211,546 A | 5/1993 | Isaacson et al. |
| 5,221,270 A | 6/1993 | Parker |
| 5,234,407 A | 8/1993 | Teirstein et al. |
| 5,234,416 A | 8/1993 | Macaulay et al. |
| 5,290,227 A | 3/1994 | Pasque |
| 5,300,112 A | 4/1994 | Barr |
| 5,308,354 A | 5/1994 | Zacca et al. |
| 5,312,341 A | 5/1994 | Turi |
| 5,344,443 A | 9/1994 | Palma et al. |
| 5,346,458 A | 9/1994 | Affeld |
| 5,346,568 A | 9/1994 | Gsellmann |
| 5,360,317 A | 11/1994 | Clausen et al. |
| 5,376,114 A | 12/1994 | Jarvik |
| 5,393,197 A | 2/1995 | Lemont et al. |
| 5,393,207 A | 2/1995 | Maher et al. |
| 5,405,341 A | 4/1995 | Martin |
| 5,405,383 A | 4/1995 | Barr |
| 5,437,541 A | 8/1995 | Vainrub |
| 5,449,342 A | 9/1995 | Hirose et al. |
| 5,458,459 A | 10/1995 | Hubbard et al. |
| 5,490,763 A | 2/1996 | Abrams et al. |
| 5,505,701 A | 4/1996 | Anaya Fernandez De Lomana |
| 5,527,159 A | 6/1996 | Bozeman et al. |
| 5,533,957 A | 7/1996 | Aldea |
| 5,534,287 A | 7/1996 | Lukic |
| 5,554,114 A | 9/1996 | Wallace et al. |
| 5,588,812 A | 12/1996 | Taylor et al. |
| 5,601,418 A | 2/1997 | Ohara et al. |
| 5,609,574 A | 3/1997 | Kaplan et al. |
| 5,613,476 A | 3/1997 | Oi |
| 5,613,935 A | 3/1997 | Jarvik |
| 5,643,226 A | 7/1997 | Cosgrove et al. |
| 5,678,306 A | 10/1997 | Bozeman et al. |
| 5,692,882 A | 12/1997 | Bozeman et al. |
| 5,702,418 A | 12/1997 | Ravenscroft |
| 5,704,926 A | 1/1998 | Sutton |
| 5,707,218 A | 1/1998 | Maher et al. |
| 5,722,930 A | 3/1998 | Larson et al. |
| 5,725,513 A | 3/1998 | Ju et al. |
| 5,725,570 A | 3/1998 | Heath |
| 5,730,628 A | 3/1998 | Hawkins |
| 5,735,897 A | 4/1998 | Buirge |
| 5,738,649 A | 4/1998 | Macoviak |
| 5,741,234 A | 4/1998 | Aboul-Hosn |
| 5,741,429 A | 4/1998 | Donadio et al. |
| 5,746,709 A | 5/1998 | Rom et al. |
| 5,749,855 A | 5/1998 | Reitan |
| 5,755,784 A | 5/1998 | Jarvik |
| 5,776,111 A | 7/1998 | Tesio |
| 5,776,161 A | 7/1998 | Globerman |
| 5,776,190 A | 7/1998 | Jarvis |

(56) References Cited

U.S. PATENT DOCUMENTS

| | | |
|---|---|---|
| 5,779,721 A | 7/1998 | Nash |
| 5,807,311 A | 9/1998 | Palestrant |
| 5,814,011 A | 9/1998 | Corace |
| 5,824,070 A | 10/1998 | Jarvik |
| 5,851,174 A | 12/1998 | Jarvik et al. |
| 5,859,482 A | 1/1999 | Crowell et al. |
| 5,868,702 A | 2/1999 | Stevens et al. |
| 5,868,703 A | 2/1999 | Bertolero et al. |
| 5,888,241 A | 3/1999 | Jarvik |
| 5,888,242 A | 3/1999 | Antaki et al. |
| 5,911,685 A | 6/1999 | Siess et al. |
| 5,921,913 A | 7/1999 | Siess |
| 5,941,813 A | 8/1999 | Sievers et al. |
| 5,951,263 A | 9/1999 | Taylor et al. |
| 5,957,941 A | 9/1999 | Ream |
| 5,964,694 A | 10/1999 | Siess et al. |
| 6,007,478 A | 12/1999 | Siess et al. |
| 6,007,479 A | 12/1999 | Rottenberg et al. |
| 6,015,272 A | 1/2000 | Antaki et al. |
| 6,015,434 A | 1/2000 | Yamane |
| 6,018,208 A | 1/2000 | Maher et al. |
| 6,027,863 A | 2/2000 | Donadio |
| 6,056,705 A | 5/2000 | Stigar-Brown |
| 6,056,719 A | 5/2000 | Mickley |
| 6,058,593 A | 5/2000 | Siess |
| 6,059,760 A | 5/2000 | Sandmore et al. |
| 6,068,610 A | 5/2000 | Ellis et al. |
| 6,071,093 A | 6/2000 | Hart |
| 6,083,260 A | 7/2000 | Aboul-Hosn |
| 6,086,527 A | 7/2000 | Talpade |
| 6,086,570 A | 7/2000 | Aboul-Hosn et al. |
| 6,106,494 A | 8/2000 | Saravia et al. |
| 6,113,536 A | 9/2000 | Aboul-Hosn et al. |
| 6,123,659 A | 9/2000 | Le Blanc et al. |
| 6,123,725 A | 9/2000 | Aboul-Hosn |
| 6,132,363 A | 10/2000 | Freed et al. |
| 6,136,025 A | 10/2000 | Barbut et al. |
| 6,139,487 A | 10/2000 | Siess |
| 6,152,704 A | 11/2000 | Aboul-Hosn et al. |
| 6,162,194 A | 12/2000 | Shipp |
| 6,176,822 B1 | 1/2001 | Nix et al. |
| 6,176,848 B1 | 1/2001 | Rau et al. |
| 6,186,665 B1 | 2/2001 | Maher et al. |
| 6,190,304 B1 | 2/2001 | Downey et al. |
| 6,190,537 B1 | 2/2001 | Kanataev et al. |
| 6,200,260 B1 | 3/2001 | Bolling |
| 6,210,133 B1 | 4/2001 | Aboul-Hosn et al. |
| 6,210,318 B1 | 4/2001 | Lederman |
| 6,210,397 B1 | 4/2001 | Aboul-Hosn et al. |
| 6,214,846 B1 | 4/2001 | Elliott |
| 6,217,541 B1 | 4/2001 | Yu |
| 6,227,797 B1 | 5/2001 | Watterson et al. |
| 6,228,063 B1 | 5/2001 | Aboul-Hosn |
| 6,234,960 B1 | 5/2001 | Aboul-Hosn et al. |
| 6,234,995 B1 | 5/2001 | Peacock |
| 6,244,835 B1 | 6/2001 | Antaki |
| 6,245,007 B1 | 6/2001 | Bedingham et al. |
| 6,245,026 B1 | 6/2001 | Campbell et al. |
| 6,247,892 B1 | 6/2001 | Kazatchkov et al. |
| 6,248,091 B1 | 6/2001 | Voelker |
| 6,254,359 B1 | 7/2001 | Aber |
| 6,254,564 B1 | 7/2001 | Wilk et al. |
| 6,287,319 B1 | 9/2001 | Aboul-Hosn et al. |
| 6,287,336 B1 | 9/2001 | Globerman et al. |
| 6,295,877 B1 | 10/2001 | Aboul-Hosn et al. |
| 6,299,635 B1 | 10/2001 | Frantzen |
| 6,305,962 B1 | 10/2001 | Maher et al. |
| 6,387,037 B1 | 5/2002 | Bolling et al. |
| 6,395,026 B1 | 5/2002 | Aboul-Hosn et al. |
| 6,413,222 B1 | 7/2002 | Pantages et al. |
| 6,422,990 B1 | 7/2002 | Prem |
| 6,425,007 B1 | 7/2002 | Messinger |
| 6,428,464 B1 | 8/2002 | Bolling |
| 6,447,441 B1 | 9/2002 | Yu et al. |
| 6,454,775 B1 | 9/2002 | Demarais et al. |
| 6,468,298 B1 | 10/2002 | Pelton |
| 6,503,224 B1 | 1/2003 | Forman et al. |
| 6,508,777 B1 | 1/2003 | Macoviak et al. |
| 6,508,787 B2 | 1/2003 | Erbel et al. |
| 6,517,315 B2 | 2/2003 | Belady |
| 6,517,528 B1 | 2/2003 | Pantages et al. |
| 6,527,699 B1 | 3/2003 | Goldowsky |
| 6,532,964 B2 | 3/2003 | Aboul-Hosn et al. |
| 6,533,716 B1 | 3/2003 | Schmitz-Rode et al. |
| 6,544,216 B1 | 4/2003 | Sammler et al. |
| 6,547,519 B2 | 4/2003 | Deblanc et al. |
| 6,565,588 B1 | 5/2003 | Clement et al. |
| 6,565,598 B1 | 5/2003 | Lootz |
| 6,609,883 B2 | 8/2003 | Woodard et al. |
| 6,610,004 B2 | 8/2003 | Viole et al. |
| 6,613,008 B2 | 9/2003 | Aboul-Hosn et al. |
| 6,616,323 B2 | 9/2003 | McGill |
| 6,623,420 B2 | 9/2003 | Reich et al. |
| 6,623,475 B1 | 9/2003 | Siess |
| 6,641,093 B2 | 11/2003 | Coudrais |
| 6,641,558 B1 | 11/2003 | Aboul-Hosn et al. |
| 6,645,241 B1 | 11/2003 | Strecker |
| 6,652,548 B2 | 11/2003 | Evans et al. |
| 6,660,014 B2 | 12/2003 | Demarais et al. |
| 6,673,105 B1 | 1/2004 | Chen |
| 6,692,318 B2 | 2/2004 | McBride |
| 6,702,830 B1 | 3/2004 | Demarais et al. |
| 6,709,418 B1 | 3/2004 | Aboul-Hosn et al. |
| 6,716,189 B1 | 4/2004 | Jarvik et al. |
| 6,749,598 B1 | 6/2004 | Keren et al. |
| 6,776,578 B2 | 8/2004 | Belady |
| 6,776,794 B1 | 8/2004 | Hong et al. |
| 6,783,328 B2 | 8/2004 | Lucke et al. |
| 6,790,171 B1 | 9/2004 | Gruendeman et al. |
| 6,794,784 B2 | 9/2004 | Takahashi et al. |
| 6,794,789 B2 | 9/2004 | Siess et al. |
| 6,814,713 B2 | 11/2004 | Aboul-Hosn et al. |
| 6,817,836 B2 | 11/2004 | Nose et al. |
| 6,818,001 B2 | 11/2004 | Wulfman et al. |
| 6,866,625 B1 | 3/2005 | Ayre et al. |
| 6,866,805 B2 | 3/2005 | Hong et al. |
| 6,887,215 B2 | 5/2005 | McWeeney |
| 6,889,082 B2 | 5/2005 | Bolling et al. |
| 6,901,289 B2 | 5/2005 | Dahl et al. |
| 6,926,662 B1 | 8/2005 | Aboul-Hosn et al. |
| 6,935,344 B1 | 8/2005 | Aboul-Hosn et al. |
| 6,942,611 B2 | 9/2005 | Siess |
| 6,949,066 B2 | 9/2005 | Bearnson et al. |
| 6,966,748 B2 | 11/2005 | Woodard et al. |
| 6,972,956 B2 | 12/2005 | Franz et al. |
| 6,974,436 B1 | 12/2005 | Aboul-Hosn et al. |
| 6,981,942 B2 | 1/2006 | Khaw et al. |
| 6,984,392 B2 | 1/2006 | Bechert et al. |
| 7,010,954 B2 | 3/2006 | Siess et al. |
| 7,011,620 B1 | 3/2006 | Siess |
| 7,014,417 B2 | 3/2006 | Salomon |
| 7,022,100 B1 * | 4/2006 | Aboul-Hosn ....... A61M 60/865 604/6.11 |
| 7,027,875 B2 | 4/2006 | Siess et al. |
| 7,037,069 B2 | 5/2006 | Arnold et al. |
| 7,070,555 B2 | 7/2006 | Siess |
| 7,122,019 B1 | 10/2006 | Kesten et al. |
| 7,125,376 B2 | 10/2006 | Viole et al. |
| 7,144,365 B2 | 12/2006 | Bolling et al. |
| 7,150,711 B2 | 12/2006 | Nusser et al. |
| 7,160,243 B2 | 1/2007 | Medvedev |
| 7,172,551 B2 | 2/2007 | Leasure |
| 7,175,588 B2 | 2/2007 | Morello |
| 7,229,258 B2 | 6/2007 | Wood et al. |
| 7,241,257 B1 | 7/2007 | Ainsworth et al. |
| 7,262,531 B2 | 8/2007 | Li et al. |
| 7,264,606 B2 | 9/2007 | Jarvik et al. |
| 7,267,667 B2 | 9/2007 | Houde et al. |
| 7,284,956 B2 | 10/2007 | Nose et al. |
| 7,288,111 B1 | 10/2007 | Holloway et al. |
| 7,290,929 B2 | 11/2007 | Smith et al. |
| 7,329,236 B2 | 2/2008 | Kesten et al. |
| 7,331,921 B2 | 2/2008 | Viole et al. |
| 7,335,192 B2 | 2/2008 | Keren et al. |

(56) References Cited

U.S. PATENT DOCUMENTS

| | | |
|---|---|---|
| 7,341,570 B2 | 3/2008 | Keren et al. |
| 7,381,179 B2 | 6/2008 | Aboul-Hosn et al. |
| 7,393,181 B2 | 7/2008 | McBride et al. |
| 7,469,716 B2 | 12/2008 | Parrino et al. |
| 7,491,163 B2 | 2/2009 | Viole et al. |
| 7,534,258 B2 | 5/2009 | Gomez et al. |
| 7,605,298 B2 | 10/2009 | Bechert et al. |
| 7,619,560 B2 | 11/2009 | Penna et al. |
| 7,633,193 B2 | 12/2009 | Masoudipour et al. |
| 7,645,225 B2 | 1/2010 | Medvedev et al. |
| 7,657,324 B2 | 2/2010 | Westlund et al. |
| 7,682,673 B2 | 3/2010 | Houston et al. |
| 7,722,568 B2 | 5/2010 | Lenker et al. |
| 7,731,675 B2 | 6/2010 | Aboul-Hosn et al. |
| 7,736,296 B2 | 6/2010 | Siess et al. |
| 7,758,521 B2 | 7/2010 | Morris et al. |
| 7,766,892 B2 | 8/2010 | Keren et al. |
| 7,780,628 B1 | 8/2010 | Keren et al. |
| 7,785,246 B2 | 8/2010 | Aboul-Hosn et al. |
| 7,811,279 B2 | 10/2010 | John |
| 7,819,833 B2 | 10/2010 | Ainsworth et al. |
| 7,820,205 B2 | 10/2010 | Takakusagi et al. |
| 7,828,710 B2 | 11/2010 | Shifflette |
| 7,842,976 B2 | 11/2010 | Fujii et al. |
| 7,918,828 B2 | 4/2011 | Lundgaard et al. |
| 7,927,068 B2 | 4/2011 | McBride et al. |
| 7,935,102 B2 | 5/2011 | Breznock et al. |
| 7,942,804 B2 | 5/2011 | Khaw |
| 7,942,844 B2 | 5/2011 | Moberg et al. |
| 7,955,365 B2 | 6/2011 | Doty |
| 7,993,259 B2 | 8/2011 | Kang et al. |
| 7,998,054 B2 | 8/2011 | Bolling |
| 7,998,190 B2 | 8/2011 | Gharib et al. |
| 8,012,079 B2 | 9/2011 | Delgado et al. |
| 8,025,647 B2 | 9/2011 | Siess et al. |
| 8,079,948 B2 | 12/2011 | Shifflette |
| 8,110,267 B2 | 2/2012 | Houston et al. |
| 8,114,008 B2 | 2/2012 | Hidaka et al. |
| 8,123,669 B2 | 2/2012 | Siess et al. |
| 8,177,703 B2 | 5/2012 | Smith et al. |
| 8,206,350 B2 | 6/2012 | Mann et al. |
| 8,209,015 B2 | 6/2012 | Glenn |
| 8,216,122 B2 | 7/2012 | Kung et al. |
| 8,235,943 B2 | 8/2012 | Breznock et al. |
| 8,236,040 B2 | 8/2012 | Mayberry et al. |
| 8,236,044 B2 | 8/2012 | Robaina |
| 8,255,050 B2 | 8/2012 | Mohl |
| 8,257,312 B2 | 9/2012 | Duffy |
| 8,262,619 B2 | 9/2012 | Chebator et al. |
| 8,277,470 B2 | 10/2012 | Demarais et al. |
| 8,317,715 B2 | 11/2012 | Belleville et al. |
| 8,329,913 B2 | 12/2012 | Murata et al. |
| 8,333,687 B2 | 12/2012 | Farnan et al. |
| 8,348,991 B2 | 1/2013 | Weber et al. |
| 8,364,278 B2 | 1/2013 | Pianca et al. |
| 8,376,707 B2 | 2/2013 | McBride et al. |
| 8,382,818 B2 | 2/2013 | Davis et al. |
| 8,388,565 B2 | 3/2013 | Shifflette |
| 8,409,128 B2 | 4/2013 | Ferrari |
| 8,414,645 B2 | 4/2013 | Dwork et al. |
| 8,439,859 B2 | 5/2013 | Pfeffer et al. |
| 8,449,443 B2 | 5/2013 | Rodefeld et al. |
| 8,485,961 B2 | 7/2013 | Campbell et al. |
| 8,489,190 B2 | 7/2013 | Pfeffer et al. |
| 8,535,211 B2 | 9/2013 | Campbell et al. |
| 8,540,615 B2 | 9/2013 | Aboul-Hosn et al. |
| 8,545,379 B2 | 10/2013 | Marseille et al. |
| 8,545,380 B2 | 10/2013 | Farnan et al. |
| 8,579,858 B2 | 11/2013 | Reitan et al. |
| 8,585,572 B2 | 11/2013 | Mehmanesh |
| 8,591,393 B2 | 11/2013 | Walters et al. |
| 8,597,170 B2 | 12/2013 | Walters et al. |
| 8,617,239 B2 | 12/2013 | Reitan |
| 8,684,904 B2 | 4/2014 | Campbell et al. |
| 8,690,749 B1 | 4/2014 | Nunez |
| 8,721,516 B2 | 5/2014 | Scheckel |
| 8,721,517 B2 | 5/2014 | Zeng et al. |
| 8,727,959 B2 | 5/2014 | Reitan et al. |
| 8,734,331 B2 | 5/2014 | Evans et al. |
| 8,734,334 B2 | 5/2014 | Haramaty et al. |
| 8,784,441 B2 | 7/2014 | Rosenbluth et al. |
| 8,790,236 B2 | 7/2014 | Larose et al. |
| 8,795,576 B2 | 8/2014 | Tao et al. |
| 8,801,590 B2 | 8/2014 | Mohl |
| 8,814,776 B2 | 8/2014 | Hastie et al. |
| 8,814,933 B2 | 8/2014 | Siess |
| 8,849,398 B2 | 9/2014 | Evans et al. |
| 8,944,748 B2 | 2/2015 | Liebing |
| 8,992,406 B2 | 3/2015 | Corbett |
| 8,998,792 B2 | 4/2015 | Scheckel |
| 9,028,216 B2 | 5/2015 | Schumacher et al. |
| 9,089,634 B2 | 7/2015 | Schumacher et al. |
| 9,089,670 B2 | 7/2015 | Scheckel |
| 9,162,017 B2 | 10/2015 | Evans et al. |
| 9,217,442 B2 | 12/2015 | Wiessler et al. |
| 9,308,302 B2 | 4/2016 | Zeng |
| 9,314,558 B2 | 4/2016 | Er |
| 9,327,067 B2 | 5/2016 | Zeng et al. |
| 9,328,741 B2 | 5/2016 | Liebing |
| 9,358,330 B2 | 6/2016 | Schumacher |
| 2002/0107506 A1 | 8/2002 | McGuckin et al. |
| 2002/0111663 A1 | 8/2002 | Dahl et al. |
| 2002/0151761 A1 | 10/2002 | Viole et al. |
| 2002/0169413 A1 | 11/2002 | Keren et al. |
| 2003/0018380 A1 | 1/2003 | Craig et al. |
| 2003/0023201 A1 | 1/2003 | Aboul-Hosn et al. |
| 2003/0100816 A1 | 5/2003 | Siess |
| 2003/0135086 A1 | 7/2003 | Khaw et al. |
| 2003/0187322 A1 | 10/2003 | Siess |
| 2003/0205233 A1 | 11/2003 | Aboul-Hosn et al. |
| 2003/0208097 A1 | 11/2003 | Aboul-Hosn et al. |
| 2003/0231959 A1 | 12/2003 | Snider |
| 2004/0019251 A1 | 1/2004 | Viole et al. |
| 2004/0044266 A1 | 3/2004 | Siess et al. |
| 2004/0101406 A1 | 5/2004 | Hoover |
| 2004/0113502 A1 | 6/2004 | Li et al. |
| 2004/0236173 A1 | 11/2004 | Viole et al. |
| 2005/0049664 A1 | 3/2005 | Harris et al. |
| 2005/0049696 A1 | 3/2005 | Siess et al. |
| 2005/0085683 A1 | 4/2005 | Bolling et al. |
| 2005/0090883 A1 | 4/2005 | Westlund et al. |
| 2005/0095124 A1 | 5/2005 | Arnold et al. |
| 2005/0113631 A1 | 5/2005 | Bolling et al. |
| 2005/0135942 A1 | 6/2005 | Wood et al. |
| 2005/0165466 A1 | 7/2005 | Morris et al. |
| 2005/0250975 A1 | 11/2005 | Carrier et al. |
| 2005/0277912 A1 | 12/2005 | John |
| 2006/0005886 A1 | 1/2006 | Parrino et al. |
| 2006/0018943 A1 | 1/2006 | Bechert et al. |
| 2006/0036127 A1 | 2/2006 | Delgado et al. |
| 2006/0058869 A1 | 3/2006 | Olson et al. |
| 2006/0062672 A1 | 3/2006 | McBride et al. |
| 2006/0063965 A1 | 3/2006 | Aboul-Hosn et al. |
| 2006/0089521 A1 | 4/2006 | Chang |
| 2006/0155158 A1 | 7/2006 | Aboul-Hosn |
| 2006/0264695 A1 | 11/2006 | Viole et al. |
| 2006/0270894 A1 | 11/2006 | Viole et al. |
| 2007/0100314 A1 | 5/2007 | Keren et al. |
| 2007/0156006 A1 | 7/2007 | Smith et al. |
| 2007/0203442 A1 | 8/2007 | Bechert et al. |
| 2007/0208298 A1 | 9/2007 | Ainsworth et al. |
| 2007/0233270 A1 | 10/2007 | Weber et al. |
| 2007/0282417 A1 | 12/2007 | Houston et al. |
| 2008/0004645 A1 | 1/2008 | To et al. |
| 2008/0004690 A1 | 1/2008 | Robaina |
| 2008/0031953 A1 | 2/2008 | Takakusagi et al. |
| 2008/0093764 A1 | 4/2008 | Ito et al. |
| 2008/0103442 A1 | 5/2008 | Kesten et al. |
| 2008/0103516 A1 | 5/2008 | Wulfman et al. |
| 2008/0103591 A1 | 5/2008 | Siess |
| 2008/0114339 A1 | 5/2008 | McBride et al. |
| 2008/0119943 A1 | 5/2008 | Armstrong et al. |
| 2008/0132748 A1 | 6/2008 | Shifflette |
| 2008/0275290 A1 | 11/2008 | Viole et al. |

(56) References Cited

U.S. PATENT DOCUMENTS

| | | |
|---|---|---|
| 2008/0306327 A1 | 12/2008 | Shifflette |
| 2009/0018567 A1 | 1/2009 | Escudero et al. |
| 2009/0023975 A1 | 1/2009 | Marseille et al. |
| 2009/0024085 A1 | 1/2009 | To et al. |
| 2009/0060743 A1 | 3/2009 | McBride et al. |
| 2009/0062597 A1 | 3/2009 | Shifflette |
| 2009/0073037 A1 | 3/2009 | Penna et al. |
| 2009/0093764 A1* | 4/2009 | Pfeffer ............... A61M 60/82 604/151 |
| 2009/0093765 A1 | 4/2009 | Glenn |
| 2009/0093796 A1 | 4/2009 | Pfeffer et al. |
| 2009/0099638 A1 | 4/2009 | Grewe |
| 2009/0112312 A1 | 4/2009 | Larose et al. |
| 2009/0118567 A1 | 5/2009 | Siess |
| 2009/0163864 A1 | 6/2009 | Breznock et al. |
| 2009/0167679 A1 | 7/2009 | Klier et al. |
| 2009/0171137 A1 | 7/2009 | Farnan et al. |
| 2009/0182188 A1 | 7/2009 | Marseille et al. |
| 2009/0234378 A1 | 9/2009 | Escudero et al. |
| 2010/0016960 A1 | 1/2010 | Bolling |
| 2010/0030186 A1 | 2/2010 | Stivland |
| 2010/0041939 A1 | 2/2010 | Siess |
| 2010/0047099 A1 | 2/2010 | Miyazaki et al. |
| 2010/0087773 A1 | 4/2010 | Ferrari |
| 2010/0127871 A1 | 5/2010 | Pontin |
| 2010/0191035 A1 | 7/2010 | Kang et al. |
| 2010/0197994 A1 | 8/2010 | Mehmanesh |
| 2010/0210895 A1 | 8/2010 | Aboul-Hosn et al. |
| 2010/0268017 A1 | 10/2010 | Siess et al. |
| 2010/0274330 A1 | 10/2010 | Burwell et al. |
| 2010/0286210 A1 | 11/2010 | Murata et al. |
| 2010/0286791 A1 | 11/2010 | Goldsmith |
| 2011/0004045 A1 | 1/2011 | Larsen et al. |
| 2011/0004046 A1* | 1/2011 | Campbell ........... A61M 60/422 600/16 |
| 2011/0004291 A1 | 1/2011 | Davis et al. |
| 2011/0021865 A1 | 1/2011 | Aboul-Hosn et al. |
| 2011/0034874 A1 | 2/2011 | Reitan et al. |
| 2011/0071338 A1 | 3/2011 | McBride et al. |
| 2011/0076439 A1 | 3/2011 | Zeilon |
| 2011/0152906 A1 | 6/2011 | Escudero et al. |
| 2011/0152907 A1 | 6/2011 | Escudero et al. |
| 2011/0236210 A1 | 9/2011 | McBride et al. |
| 2011/0237863 A1 | 9/2011 | Ricci et al. |
| 2011/0238172 A1 | 9/2011 | Akdis |
| 2011/0257462 A1 | 10/2011 | Rodefeld et al. |
| 2011/0270182 A1 | 11/2011 | Breznock et al. |
| 2011/0275884 A1 | 11/2011 | Scheckel |
| 2012/0004495 A1 | 1/2012 | Bolling et al. |
| 2012/0029265 A1 | 2/2012 | Larose et al. |
| 2012/0045352 A1 | 2/2012 | Lawyer et al. |
| 2012/0059213 A1 | 3/2012 | Spence et al. |
| 2012/0142994 A1 | 6/2012 | Toellner |
| 2012/0172654 A1 | 7/2012 | Bates |
| 2012/0172655 A1 | 7/2012 | Campbell et al. |
| 2012/0172656 A1 | 7/2012 | Walters et al. |
| 2012/0178985 A1 | 7/2012 | Walters et al. |
| 2012/0178986 A1 | 7/2012 | Campbell et al. |
| 2012/0184803 A1 | 7/2012 | Simon et al. |
| 2012/0224970 A1 | 9/2012 | Schumacher et al. |
| 2012/0226097 A1 | 9/2012 | Smith et al. |
| 2012/0234411 A1 | 9/2012 | Scheckel et al. |
| 2012/0237357 A1 | 9/2012 | Schumacher et al. |
| 2012/0245404 A1 | 9/2012 | Smith et al. |
| 2012/0265002 A1 | 10/2012 | Roehn et al. |
| 2013/0031936 A1 | 2/2013 | Goncalves Ferreira et al. |
| 2013/0039465 A1 | 2/2013 | Okuno |
| 2013/0041202 A1 | 2/2013 | Toellner et al. |
| 2013/0053622 A1 | 2/2013 | Corbett |
| 2013/0053623 A1 | 2/2013 | Evans et al. |
| 2013/0066140 A1 | 3/2013 | McBride et al. |
| 2013/0085318 A1 | 4/2013 | Toellner et al. |
| 2013/0085319 A1 | 4/2013 | Evans et al. |
| 2013/0096364 A1 | 4/2013 | Reichenbach et al. |
| 2013/0103063 A1 | 4/2013 | Escudero et al. |
| 2013/0106212 A1 | 5/2013 | Nakazumi et al. |
| 2013/0129503 A1 | 5/2013 | McBride et al. |
| 2013/0138205 A1 | 5/2013 | Kushwaha et al. |
| 2013/0204362 A1 | 8/2013 | Toellner et al. |
| 2013/0209292 A1 | 8/2013 | Baykut et al. |
| 2013/0237744 A1 | 9/2013 | Pfeffer et al. |
| 2013/0245360 A1 | 9/2013 | Schumacher et al. |
| 2013/0303831 A1 | 11/2013 | Evans et al. |
| 2013/0303969 A1 | 11/2013 | Keenan et al. |
| 2013/0303970 A1 | 11/2013 | Keenan et al. |
| 2013/0331639 A1 | 12/2013 | Campbell et al. |
| 2013/0345492 A1 | 12/2013 | Pfeffer et al. |
| 2014/0005467 A1 | 1/2014 | Farnan et al. |
| 2014/0010686 A1 | 1/2014 | Tanner et al. |
| 2014/0012065 A1 | 1/2014 | Fitzgerald et al. |
| 2014/0067057 A1 | 3/2014 | Callaway et al. |
| 2014/0088455 A1 | 3/2014 | Christensen et al. |
| 2014/0148638 A1 | 5/2014 | Larose et al. |
| 2014/0163664 A1 | 6/2014 | Goldsmith |
| 2014/0255176 A1 | 9/2014 | Bredenbreuker et al. |
| 2014/0275725 A1 | 9/2014 | Schenck et al. |
| 2014/0275726 A1 | 9/2014 | Zeng |
| 2014/0301822 A1 | 10/2014 | Scheckel |
| 2014/0303596 A1 | 10/2014 | Schumacher et al. |
| 2015/0025558 A1 | 1/2015 | Wulfman et al. |
| 2015/0051435 A1 | 2/2015 | Siess et al. |
| 2015/0051436 A1 | 2/2015 | Spanier et al. |
| 2015/0080743 A1 | 3/2015 | Siess et al. |
| 2015/0087890 A1 | 3/2015 | Spanier et al. |
| 2015/0141738 A1 | 5/2015 | Toellner et al. |
| 2015/0141739 A1 | 5/2015 | Hsu et al. |
| 2015/0151032 A1 | 6/2015 | Voskoboynikov et al. |
| 2015/0209498 A1 | 7/2015 | Franano et al. |
| 2015/0224970 A1 | 8/2015 | Yasui et al. |
| 2015/0250935 A1 | 9/2015 | Anderson et al. |
| 2015/0290372 A1 | 10/2015 | Muller et al. |
| 2015/0343179 A1 | 12/2015 | Schumacher et al. |
| 2016/0184500 A1 | 6/2016 | Zeng |
| 2016/0250399 A1 | 9/2016 | Tiller et al. |
| 2016/0250400 A1 | 9/2016 | Schumacher |
| 2016/0256620 A1 | 9/2016 | Scheckel et al. |

FOREIGN PATENT DOCUMENTS

| | | | |
|---|---|---|---|
| CA | 2367469 | A1 | 10/2000 |
| CA | 2407938 | A1 | 11/2001 |
| CA | 2480467 | A1 | 8/2003 |
| CA | 2701870 | A1 | 4/2009 |
| DE | 19613565 | C1 | 7/1997 |
| DE | 10059714 | C1 | 5/2002 |
| DE | 112004001809 | T5 | 11/2006 |
| EP | 0193762 | A2 | 9/1986 |
| EP | 0364293 | A2 | 4/1990 |
| EP | 0453234 | A1 | 10/1991 |
| EP | 0533432 | A1 | 3/1993 |
| EP | 1207934 | A2 | 5/2002 |
| EP | 1591079 | A1 | 11/2005 |
| EP | 2151257 | A1 | 2/2010 |
| EP | 2263732 | A2 | 12/2010 |
| EP | 2298374 | A1 | 3/2011 |
| EP | 2427230 | A1 | 3/2012 |
| FR | 2267800 | A1 | 11/1975 |
| GB | 886219 | A | 1/1962 |
| GB | 2239675 | A | 7/1991 |
| JP | S4823295 | | 3/1973 |
| JP | S58190448 | | 11/1983 |
| JP | H08500512 | A | 1/1996 |
| JP | H08501466 | A | 2/1996 |
| JP | H09114101 | A | 5/1997 |
| JP | 10099447 | | 4/1998 |
| JP | 2002505168 | A | 2/2002 |
| JP | 2004514506 | A | 5/2004 |
| JP | 2011000620 | A | 1/2011 |
| JP | 2011157961 | A | 8/2011 |
| NO | 0019097 | A1 | 4/2000 |
| TW | 500877 | B | 9/2002 |
| WO | 8904644 | A1 | 6/1989 |
| WO | 8905164 | A1 | 6/1989 |
| WO | 9405347 | A1 | 3/1994 |

(56) References Cited

FOREIGN PATENT DOCUMENTS

| | | |
|---|---|---|
| WO | 9406486 A1 | 3/1994 |
| WO | 9526695 A2 | 10/1995 |
| WO | 9715228 A1 | 5/1997 |
| WO | 9737697 A1 | 10/1997 |
| WO | 9737698 A1 | 10/1997 |
| WO | 9900368 A1 | 1/1999 |
| WO | 9902204 A1 | 1/1999 |
| WO | 9916387 A1 | 4/1999 |
| WO | 9937352 A1 | 7/1999 |
| WO | 9944651 A1 | 9/1999 |
| WO | 9944670 A1 | 9/1999 |
| WO | 9959652 A1 | 11/1999 |
| WO | 9965546 A1 | 12/1999 |
| WO | 0012148 A2 | 3/2000 |
| WO | 0018448 A2 | 4/2000 |
| WO | 0037139 A1 | 6/2000 |
| WO | 0038591 A2 | 7/2000 |
| WO | 0041612 A2 | 7/2000 |
| WO | 0043053 A1 | 7/2000 |
| WO | 0043062 A1 | 7/2000 |
| WO | 0045874 A1 | 8/2000 |
| WO | 0061207 A1 | 10/2000 |
| WO | 0069489 A1 | 11/2000 |
| WO | 0117581 A2 | 3/2001 |
| WO | 0124867 A1 | 4/2001 |
| WO | 0178807 A1 | 10/2001 |
| WO | 0183016 A2 | 11/2001 |
| WO | 02070039 A2 | 9/2002 |
| WO | 03048582 A1 | 6/2003 |
| WO | 03068303 A2 | 8/2003 |
| WO | 03070299 A1 | 8/2003 |
| WO | 03103745 A2 | 12/2003 |
| WO | 2005089674 A1 | 9/2005 |
| WO | 2005123158 A1 | 12/2005 |
| WO | 2006034158 A2 | 3/2006 |
| WO | 2006046779 A1 | 5/2006 |
| WO | 2006051023 A1 | 5/2006 |
| WO | 2007112033 A2 | 10/2007 |
| WO | 2008034068 A2 | 3/2008 |
| WO | 2009073037 A1 | 6/2009 |
| WO | 2009076460 A2 | 6/2009 |
| WO | 2010063494 A1 | 6/2010 |
| WO | 2010127871 A1 | 11/2010 |
| WO | 2010133567 A1 | 11/2010 |
| WO | 2010149393 A1 | 12/2010 |
| WO | 2011003043 A1 | 1/2011 |
| WO | 2011035926 A1 | 3/2011 |
| WO | 2011035927 A1 | 3/2011 |
| WO | 2011035929 A2 | 3/2011 |
| WO | 2011039091 A1 | 4/2011 |
| WO | 2011076439 A1 | 6/2011 |
| WO | 2011089022 A1 | 7/2011 |
| WO | 2012007140 A1 | 1/2012 |
| WO | 2012007141 A1 | 1/2012 |
| WO | 2012094525 A2 | 7/2012 |
| WO | 2012094534 A2 | 7/2012 |
| WO | 2013148697 A1 | 10/2013 |
| WO | 2013160407 A1 | 10/2013 |
| WO | 2013173245 A1 | 11/2013 |
| WO | 2014019274 A1 | 2/2014 |
| WO | 2015063277 A2 | 5/2015 |

OTHER PUBLICATIONS

Siess et al., "Concept, realization, and first in vitro testing of an intraarterial microaxial blood pump," Artificial Organs, 1995, pp. 644-652, vol. 19, No. 7, Blackwell Science, Inc., Boston, International Society for Artificial Organs.

Siess, "Systemanalyse und Entwicklung intravasaler Rotationspumpen zur Herzunterstlitzung", Helmholtz-Institut fur Blomedixinische Technik an der RWfH Aachen, Jun. 24, 1998, in 105 pages.

Smith EJ, et al. "First-In-Man Study of the Reitan Catheter Pump for circulatory Support in Patients Undergoing High-Risk Percutaneous Coronary Intervention," Catheter Cardiovasc Interv 2009; 73(7):859-65.

Sokolowski W., Metcalfe A, Hayashi S., Yuahia L., Raymond k,"Medical Applications of Shape Memory Polymers." Biomed Mater 2007;2(1 ):S23-S27.

Stoeckel D, Pelton A, Duerig T. Self-Expanding nitinol stents: material and design considerations European Radiology. 2004; 14:292-301.

Supplemental European Search Report received from the European Patent Office in EP Application No. EP 05799883 dated Mar. 19, 2010, 3 pages.

Takagaki et al. A Novel Miniature Ventricular Assist Device for Hemodynamic Support. ASAIO Journal 2001, pp. 412-416.

Throckmorton A, et al. ,"Flexible Impeller Blades in an Axial Flow Pump for Intravascular Cavopulmonary Assistance of the Fontan Physiology." Cardiovasc Eng Technology 2010; 1(4):244-55.

Throckmorton et al., "Uniquely shaped cardiovascular stents enhance the pressure generation of intravascular blood pumps," The Journal of Thoracic and Cardiovascular Surgery, Sep. 2012, pp. 704-709, vol. 133, No. 3.

Verkerke, Bart et al., The PUCA Pump: A Left Ventricular Assist Device, Artificial Organs 17(5): 365-368; 1993.

Verkerke, CJ et al., Numerical Simulation of the PUCA Pump, A Left Ventricular Assist Device, Abstracts of the XIXth ESAO Congress, The International Journal of Artificial Organs 15(9): 543; 1992.

Verkerke, Gijsbertus et al., Numerical Simulation of the Pulsating Catheter Pump: A Left Ventricular Assist Device, Artificial Organs 23(10): 924-931; 1999.

Wampler, Richard. K., et al., The Sternotomy Hemopump, A Second Generation Intraarterial Ventricular Assist Device; Johnson and Johnson Interventional Systems, pp. M218-223 1993.

Weber et al. , "Principles of Impella Cardiac Support," Supplemental to Cardiac Interventions Today, Aug./Sep. 2009.

Partial EP search report, dated Dec. 1, 2020, for related EP patent application No. 20187258.7 (12 pgs.).

Sharony, R. et al. Right heart support during off-pump coronary artery surgery—a multicenter study. Heart Surg Forum. 2002;5(1):13-16.

Biscarini A, Mazzolai G., Tuissi A ,"Enhanced nitinol properties for biomedical applications," Recent Patents on Biomedical Engineering 2008; 1 (3): 180-96.

Cardiovascular Diseases (CVDs) Fact Sheet No. 317. World Health Organization. [Online] Sep. 2011 http://www.who.int/mediacentre/factsheets/fs317/en/index. html, accessed on Aug. 29, 2012.

Duerig T, Pelton A, Stockel D. "An Overview of nitinol Medical Applications ," Mat Sci Eng 1999: 149-160.

European Search Report received from the European Patent Office in EP Application No. EP 05799883.3 dated May 10, 2011, 4 pages.

Extended European Search Report received from the European Patent Office in European Patent Application No. EP 07753903.9, dated Oct. 8, 2012, 7 pages.

Extended European Search Report received in European Patent Application No. 13813687.4, dated Feb. 24, 2016, in 6 pages.

Extended European Search Report received in European Patent Application No. 14 764392.8, dated Oct. 27, 2016, in 7 pages.

Extended European Search Report received in European Patent Application No. 14 779928.2, dated Oct. 7, 2016, in 6 pages.

Grech ED. Percutaneous coronary Intervention I: History and development. BMJ. 2003;326: 1080.

Hsu et al. ,"Review of Recent Patents on Foldable Ventricular Assist Devices," Recent Patents on Biomedical Engineering, 2012, pp. 208-222, vol. 5.

Ide, Hirofumi et al., Evaluation of the Pulsatility of a New Pulsatile Left Ventricular Assist Device—the Integrated Cardioassist Catheter—in Dogs, J. of Thoracic and Cardiovascular Surgery 107(2): 569-0575; Feb. 1994.

Ide, Hirofumi et al., Hemodynamic Evaluation of a New Left Ventricular Assist Device, Artificial Organs 16 (3): 286-290; 1992.

International Preliminary Examination Report from the European Patent Office received in PCT Application No. PCT/US2003/04401, mailed May 18, 2004, 4 pages.

(56) References Cited

OTHER PUBLICATIONS

International Preliminary Examination Report from the European Patent Office received in PCT Application No. PCT/US2003/04853, mailed Jul. 26, 2004, 5 pages.
International Preliminary Report on Patentability and Written Opinion of the International Searching Authority received in PCT Application No. PCT/US2005/033416, mailed Mar. 20, 2007, 7 pages.
International Preliminary Report on Patentability of the International Searching Authority received in PCT Application No. PCT/US2007/007313, mailed Sep. 23, 2008, 6 pages.
International Search Report and Written Opinion received in International Patent Application No. PCT/US2013/040798, mailed on Aug. 21, 2013, in 16 pages.
International Search Report and Written Opinion received in International Patent Application No. PCT/US2013/040799, mailed on Aug. 21, 2013, in 19 pages.
International Search Report and Written Opinion received in International Patent Application No. PCT/US2013/040809, mailed on Sep. 2, 2013, in 25 pages.
International Search Report and Written Opinion received in International Patent Application No. PCT/US2013/048332, mailed on Oct. 16, 2013, in 17 pages.
International Search Report and Written Opinion received in International Patent Application No. PCT/US2013/048343, mailed on Oct. 11, 2013, in 15 pages.
International Search Report and Written Opinion received in International Patent Application No. PCT/US2016/014371, mailed May 2, 2016, in 18 pages.
International Search Report and Written Opinion received in International Patent Application No. PCT/US2016/014379, mailed Jul. 25, 2016, in 19 pages.
International Search Report and Written Opinion received in International Patent Application No. PCT/US2016/014391, mailed May 2, 2016, in 17 pages.
International Search Report and Written Opinion received in PCT Application No. PCT/US2005/33416, mailed Dec. 11, 2006, 8 pages.
International Search Report and Written Opinion received in PCT Application No. PCT/US2007/07313, mailed Mar. 4, 2008, 6 pages.
International Search Report and Written Opinion received in PCT Application No. PCT/US2010/040847 mailed on Dec. 14, 2010, 17 pages.
International Search Report and Written Opinion received in PCT Application No. PCT/US2012/020369 mailed Jul. 30, 2012.
International Search Report and Written Opinion received in PCT Application No. PCT/US2012/020382, mailed Jul. 31, 2013.
International Search Report and Written Opinion received in PCT Application No. PCT/US2012/020383 mailed Aug. 17, 2012.
International Search Report and Written Opinion received in PCT Application No. PCT/US2012/020553 mailed Aug. 17, 2012.
International Search Report received in PCT Application No. PCT/US2003/04401, mailed Nov. 10, 2003, 9 pages.
International Search Report received in PCT Application No. PCT/US2003/04853, mailed Jul. 3, 2003, 3 pages.
Krishnamani R, DeNofrio D, Konstam MA Emerging ventricular assist devices for long-term cardiac support. Nat Rev Cardiol 2010; 7-71-6.
Mihaylov, D. et al., Evaluation of the Optimal Driving Mode During Left Ventricular Assist with Pulsatile Catheter Pump in Calves, Artificial Organs 23(12): 1117-1122; 1999.
Mihaylov, Di Miter et al., Development of a New Introduction Technique for the Pulsatile Catheter Pump, Artificial Organs 21 (5): 425-427; 1997.
Morgan NB. "Medical Shape memory alloy applications—the market and its products," Mat Sci Eng 2004; 378: 16-23.
Morsink, PLJ et al., Numerical Modelling of Blood Flow Behaviour in the Valved Catheter of the PUCA Pump, a LVAD, The International Journal of Artificial Organs 20(5): 277-284; 1997.

Nishimura et al. The enabler cannula pump: a novel circulatory support system. The International Journal of Artificial Organs, vol. 22, No. 5, 1999, pp. 317-323.
Petrini L, Migliavacca F. Biomedical Applications of Shape Memory Alloys. Journal of Metallurgy 2011.
Raess D, Weber D. Impella 2.5 J. Cardiovasc Transl Res 2009; 2 (2): 168-72.
Rakhorst Gerhard et al. In Vitro Evaluation of the Influence of Pulsatile Intraventricular Pumping on Ventricular Pressure Patterns, Artificial Organs 18(7): 494-499; 1994.
Reitan, Oyvind, et al., Hemodynamic Effects of a New Percutaneous Circulatory Support Device in a Left Ventricular Failure Model. ASAIO Journal 2003: 49:731-6.
Reitan, Oyvind, et al., Hydrodynamic Properties of a New Percutaneous Intra-aortic Axial Flow Pump. ASAIO Journal 2000. pp. 323-329.
Schmitz-Rode et al., "Axial flow catheter pump for circulatory support," Biomedizinische Technik, 2002, Band 4 7, Erganzungsband 1, Teil 1, pp. 142-143.
Schmitz-Rode, Thomas et al., "An Expandable Percutaneous Catheter Pump for Left Ventricular Support", Journal of the American College of Cardiology, vol. 45, No. 11, 2005, pp. 1856-1861.
Shabari et al.,"Improved Hemodynamics with a Novel Miniaturized Intra-Aortic Axial Flow Pump in a Porcine Model of Acute Left Ventricular Dysfunction," ASAIO Journal, 2013, pp. 240-245: vol. 59.
Sharony et al. Cardiopulmonary Support and Physiology—The Intra-Aortic Cannula Pump: A Novel Assist Device for the Acutely Failing Heart. The Journal of Thoracic and Cardiovascular Surgery, Nov. 1992, vol. 118, No. 5, pp. 924-929.
Written Opinion received in PCT Application No. PCT/US2003/04853, dated Feb. 25, 2004, 5 pages.
"In response to the Proprietor's letter of Jul. 18, 2012" from Hoffmann Eitle dated Oct. 24, 2012, Opposition, EP 2 234 658 81, Proprietor: AIS GmbH Aachen Innovative Solutions (DE), Opponent Dr. Niels Holder (DE), 7 pages.
"Response to the Summons dated Jun. 14, 2013:" from Fish & Richardson P.C., dated Oct. 7, 2013, Opposition against EP 2 047 872 81, 12 pages.
"Responsive to the Summons dated Aug. 26, 2013:" from Fish & Richardson P.C., dated Oct. 7, 2013, Opposition against EP 2 234 658 81, 9 pages.
1st Auxiliary Application dated Oct. 11, 2013, European Application No. 07019657.1, 23 pages Facts of the Case and Petitions, dated Feb. 7, 2014, European Application No. 04763480.3, 13 pages.
Aboul-Hosn et al. ,"The Hemopump: Clinical Results and Future Applications", Assisted Circulation 4, 1995, in 14 pages.
Compendium of Technical and Scientific Information for the HEMOPUMP Temporary Cardiac Assist System, Johnson & Johnson Interventional Systems, 1988, in 15 pages.
Decision on Rejection of the objection, dated Oct. 1, 2014, European Application No. 04763480.3, 3 pages.
Decision rejecting the opposition (EPC Art. 101(2), dated Oct. 1, 2014, European Application No. 07 019 657.1, 13 pages.
Dekker et al. ,"Efficacy of a New Intraaortic Propeller Pump vs the Intraaortic Balloon Pump, An Animal Study", Chest, Jun. 2003, vol. 123, No. 6, pp. 2089-2095.
Extended European Search Report received in European Patent Application No. 13813867, dated Feb. 26, 2016, in 6 pages.
Fact and Arguments from Hoffmann Eitle, Opposition, EP 2 234 658 81, Proprietor: AIS GmbH Aachen Innovative Solutions (DE), Opponent: Dr. Niels Holder (DE), dated Feb. 3, 2012; 29 pages.
Fact and Arguments from Hoffmann Eitle. Opposition, EP 2 047 872 81, Proprietor: AIS GmbH Aachen Innovative Solutions (DE), Opponent: Dr. Niels Holder (DE), dated Jun. 8, 2011; 32 pages.
Facts and Ground for the Opposition dated Oct. 17, 2012, European Application No. 04763480.3, 43 pages.
Facts of the Case and Petitions, dated Oct. 1, 2014, European Application No. 04763480.3, 16 pages.
Federal and Drug Administration 51 O(k) Summary for Predicate Device IMPELLA 2.5 (K112892), prepared Sep. 5, 2012.

(56) References Cited

OTHER PUBLICATIONS

International Preliminary Report on Patentability and Written Opinion received in International Patent Application No. PCT/US2014/020878, mailed Sep. 15, 2015, in 8 pages.
International Search Report and Written Opinion received in International Patent Application No. PCT/US2014/020878, mailed May 7, 2014, in 13 pages.
International Search Report and Written Opinion received in International Patent Application No. PCT/US2015/025960, mailed Sep. 3, 2015, in 15 pages.
International Search Report and Written Opinion received in International Patent Application No. PCT/US2015/026013, mailed Jul. 8, 2015, in 12 pages.
International Search Report and Written Opinion received in International Patent Application No. PCT/US2015/026014, mailed Jul. 15, 2015, in 13 pages.
International Search Report and Written Opinion received in International Patent Application No. PCT/US2015/026025, mailed Jul. 20, 2015, in 12 pages.
International Search Report and Written Opinion received in International Patent Application No. PCT/US2015/045370, mailed Nov. 18, 2015, in 12 pages.
JOMED Reitan Catheter Pump RCP, Feb. 18, 2003, in 4 pages.
JOMED Reitan Catheter Pump RCP, Percutaneous Circulatory Support, in 10 pages, believed to be published prior to Oct. 15, 2003.
Kunst et al. ,"Integrated unit for programmable control of the 21 F Hemopump and registration of physiological signals," Medical & Biological Engineering & Computing, Nov. 1994, pp. 694-696.
Impella CP®—Instructions for Use & Clinical Reference Manual (United States only), Abiomed, Inc., Jul. 2014, 148 pages, www.abiomed.com.
Impella LD® with the Impella® Controller—Circulatory Support System—Instructions for Use & Clinical Reference Manual (United States only), Abiomed, Inc., Sep. 2010, 132 pages, www.abiomed.com.
Minimally Invasive Cardiac Assist JOMED Catheter Pump™. in 6 pages.
Motion to dismiss the objection by Dr. Niels Holder dated Jan. 17, 2012 to EPO in European Patent No. 2 04 7 872 B 1, 12 pages.
Nullity Action against the owner of the German part DE 50 2007 005 015.6 of European patent EP 2 04 7 872 81, dated Jul. 13, 2015, in 61 pages.
Opinion on behalf of the Opponent dated Aug. 26, 2013, filed with the European Patent Office in European Application No. 04763480.3 (EP Patent No. 1 651 290 81 ), 23 pages.
Opposition by Dr. Niels Holder dated Jul. 18, 2012 to EPO in European Patent No. 2 234 658 81, 14 pages.
Opposition Opinion of EP 2 234 658, dated Jan. 20, 2014; 3 pages.
Reitan, Evaluation of a New Percutaneous Cardiac Assist Device, Department of Cardiology, Faculty of Medicine, Lund University, Sweden, 2002, in 172 pages.
Reply to the Objection by Thoratec Corporation of Oct. 17, 2012, from the European Patent Office dated Mar. 22, 2013 , European Patent No. 1 651 290, 14 pages.
Response to Memorandum of Aug. 26, 2013 with the invitation to an oral hearing, dated Oct. 11, 2013, European Patent No. 2 234 658, 28 pages.
Rothman, "The Reitan Catheter Pump: A New Versatile Approach for Hemodynamic Support", London Chest Hospital Barts & The London NHS Trust, Oct. 22-27, 2006 (TCT 2006: Transcatheter Cardiovascular Therapeutics 18 1h Annual Scientific Symposium, Final Program), in 48 pages.
Siess et al. ,"Basic Design Criteria for Rotary Blood Pumps", Rotary Blood Pumps, 2000, in 15 pages.
Siess et al. ,"From a Lab Type to a Product: A Retrospective View on Impella'S Assist Technology", Artificial Organs, 2001, vol. 25, No. 5, pp. 414-421.
Siess et al., "System analysis and development of intravascular rotation pumps for cardiac assist," Dissertation, Shaker Verlag, Aachen, 1999, 39 pages.
Sim et al. ,"Concept, Realization, and First In Vitro Testing of an Intraarterial Microaxial Blood Pump", Artificial Organs, 1995, vol. 19, No. 7, pp. 644-652.
Sim et al. ,"Hydraulic refinement of an intraarterial microaxial blood pump", The International Journal of Artificial Organs, 1995, vol. 18, No. 5, pp. 273-285.
Sim, "Systemanalyse und Entwicklung intravasaler Rotationspumpen zur Herzunterstutzung", Helmholtz-Institut fur Blomedixinische Technik an der RWTH Aachen, Jun. 24, 1998, in 105 pages.
Statement of Appeal, dated Feb. 6, 2015, European Patent No. 1 651 290, Opponent and Appellant Thoratec Corporation, 30 pages.
Stolinski et al. ,"The heart-pump interaction: effects of a microaxial blood pump," International Journal of Artificial Organs, 2002, pp. 1082-1088, vol. 25, Issue 11.
Synopse zu Anspruchen 1 bis 5 der EP 2 047 872, in 11 pages.
"Statistical Analysis and Clinical Experience with the Recover® Pump Systems", Impella CardioSystems GmbH, 2 sheets.
Abiomed—Recovering hearts. Saving lives., Impella 2.5 System, Instructions for Use, Jul. 2007 86 sheets.
Abiomed, "Impella 5.0 with the Impella Console, Circulatory Support System, Instructions for Use & Clinical Reference Manual," Jun. 2010, in 122 pages.
Barras CDJ, Myers KA. Nitinol—Its Use in vascular Surgery and Other Applications. Eur J. Vasc Endovasc Surg 2000; 19:564-9.

* cited by examiner

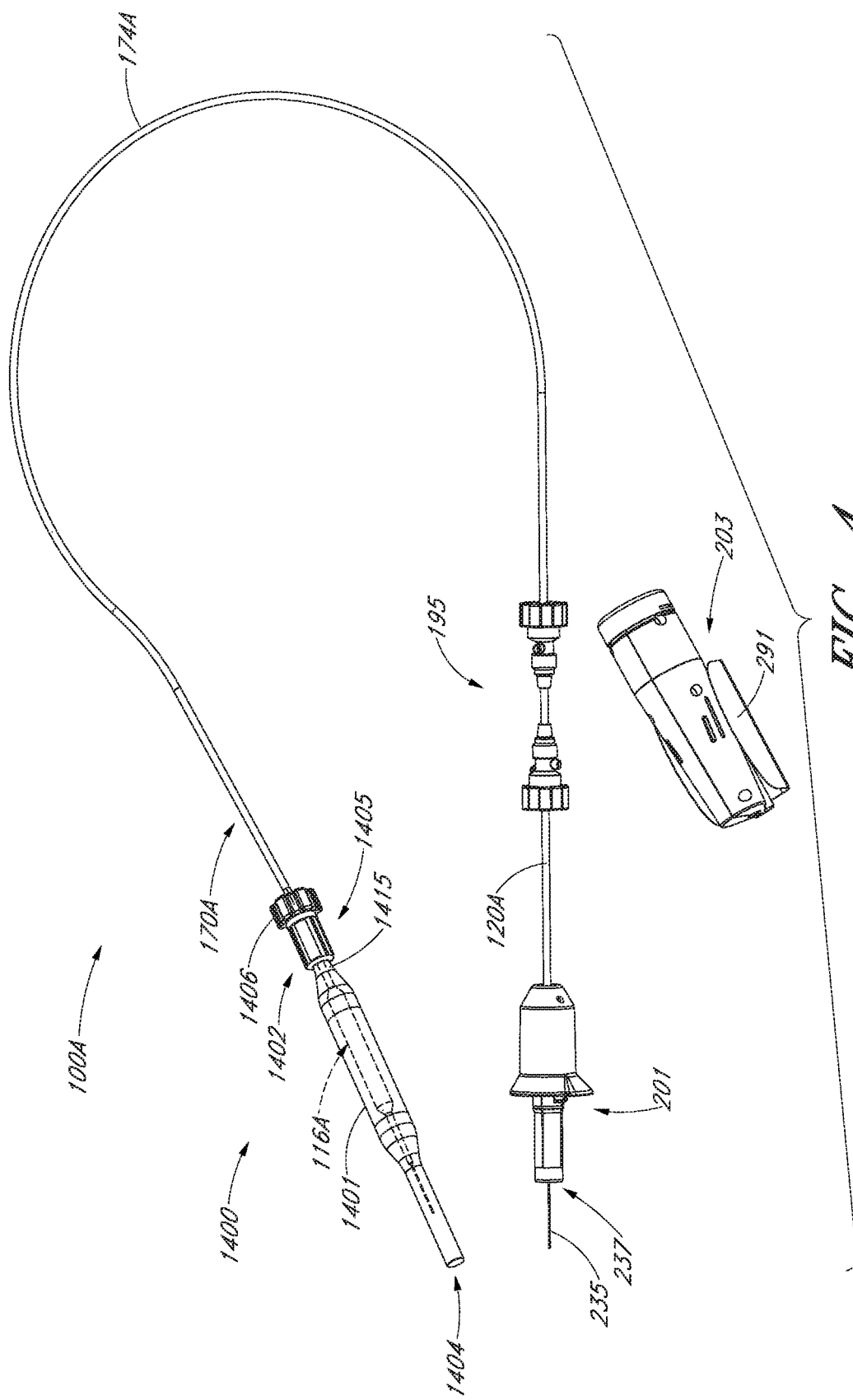

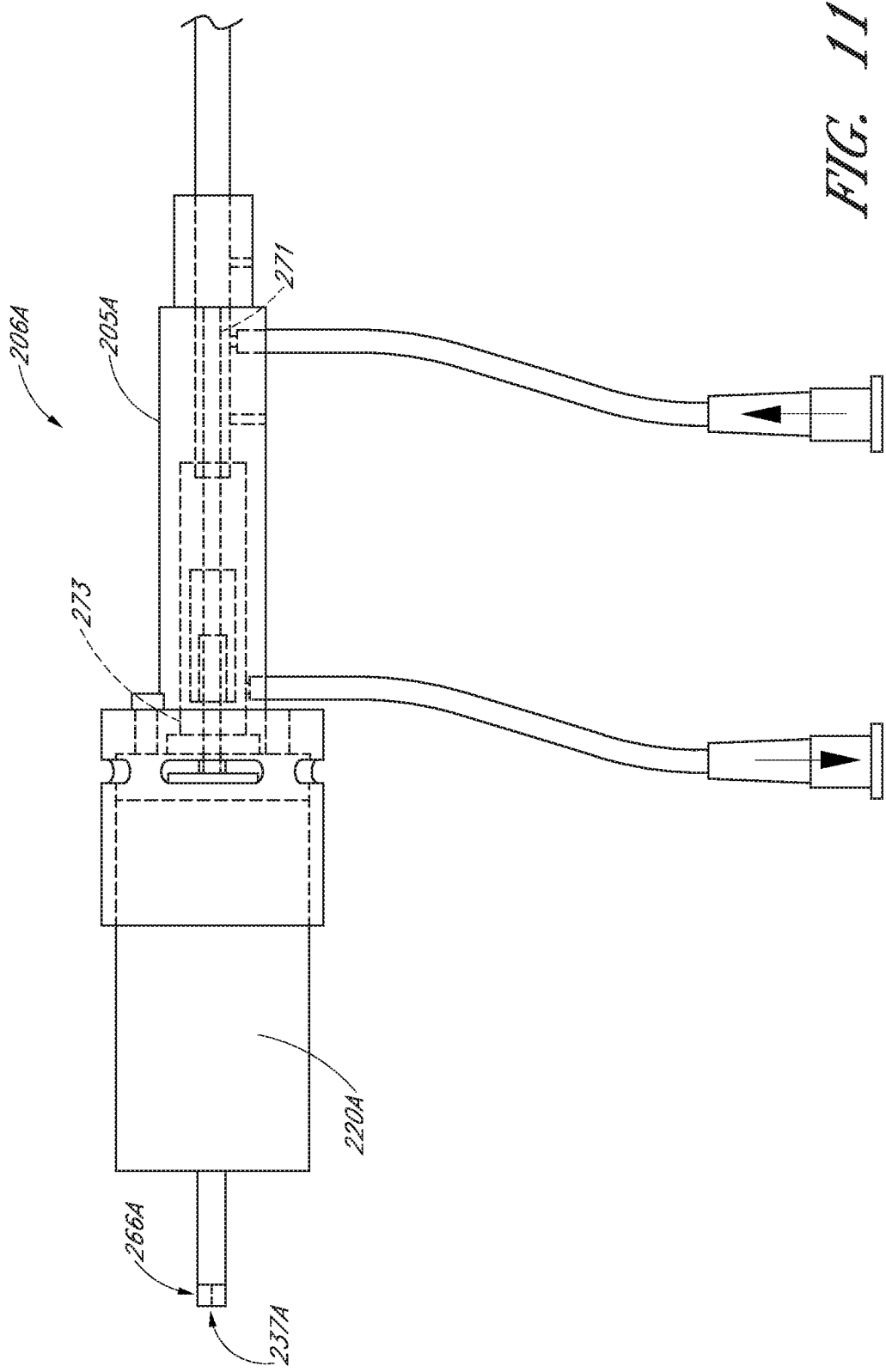

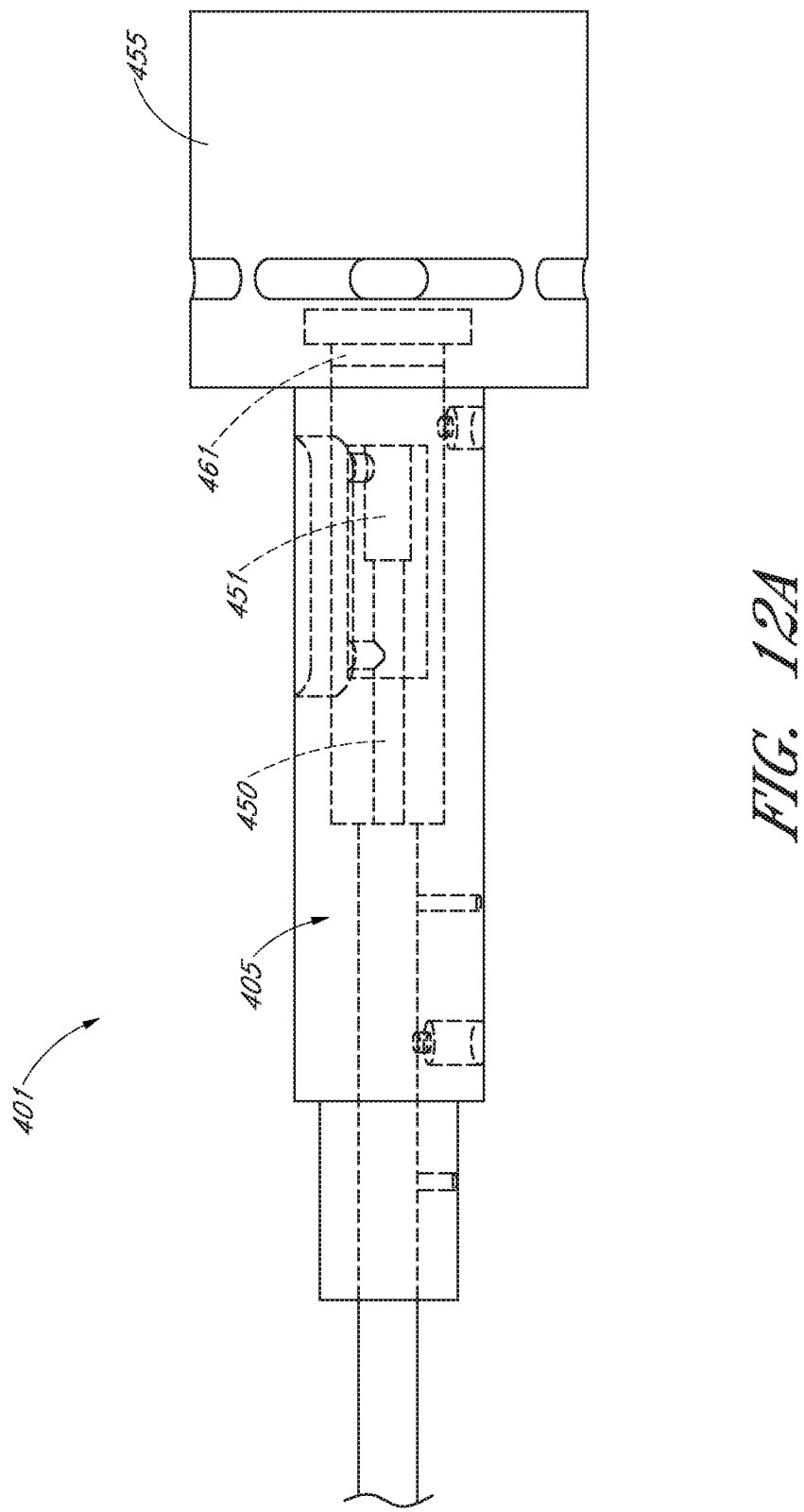

MOTOR ASSEMBLY FOR CATHETER PUMP

CROSS-REFERENCE TO RELATED APPLICATIONS

This application is a Continuation of U.S. patent application Ser. No. 16/742,129, filed Jan. 14, 2020, which is a Continuation of U.S. patent application Ser. No. 15/242,024, filed on Aug. 19, 2016, which is a Continuation of U.S. patent application Ser. No. 13/802,468, filed on Mar. 13, 2013, which claims the benefit of priority to U.S. Provisional Application No. 61/667,869, filed on Jul. 3, 2012, titled "MOTOR ASSEMBLY FOR CATHETER PUMP," the entire contents of which are incorporated herein by reference.

BACKGROUND OF THE INVENTION

Field of the Invention

This application is directed to catheter pumps for mechanical circulatory support of a heart.

Description of the Related Art

Heart disease is a major health problem that has high mortality rate. Physicians increasingly use mechanical circulatory support systems for treating heart failure. The treatment of acute heart failure requires a device that can provide support to the patient quickly. Physicians desire treatment options that can be deployed quickly and minimally-invasively.

Intra-aortic balloon pumps (IABP) are currently the most common type of circulatory support devices for treating acute heart failure. IABPs are commonly used to treat heart failure, such as to stabilize a patient after cardiogenic shock, during treatment of acute myocardial infarction (MI) or decompensated heart failure, or to support a patient during high risk percutaneous coronary intervention (PCI). Circulatory support systems may be used alone or with pharmacological treatment.

In a conventional approach, an IABP is positioned in the aorta and actuated in a counterpulsation fashion to provide partial support to the circulatory system. More recently minimally-invasive rotary blood pump have been developed in an attempt to increase the level of potential support (i.e., higher flow). A rotary blood pump is typically inserted into the body and connected to the cardiovascular system, for example, to the left ventricle and the ascending aorta to assist the pumping function of the heart. Other known applications pumping venous blood from the right ventricle to the pulmonary artery for support of the right side of the heart. An aim of acute circulatory support devices is to reduce the load on the heart muscle for a period of time, to stabilize the patient prior to heart transplant or for continuing support.

There is a need for improved mechanical circulatory support devices for treating acute heart failure. Fixed cross-section ventricular assist devices designed to provide near full heart flow rate are either too large to be advanced percutaneously (e.g., through the femoral artery without a cutdown) or provide insufficient flow.

There is a need for a pump with improved performance and clinical outcomes. There is a need for a pump that can provide elevated flow rates with reduced risk of hemolysis and thrombosis. There is a need for a pump that can be inserted minimally-invasively and provide sufficient flow rates for various indications while reducing the risk of major adverse events. In one aspect, there is a need for a heart pump that can be placed minimally-invasively, for example, through a 15 FR or 12 FR incision. In one aspect, there is a need for a heart pump that can provide an average flow rate of 4 Lpm or more during operation, for example, at 62 mmHg of head pressure. While the flow rate of a rotary pump can be increased by rotating the impeller faster, higher rotational speeds are known to increase the risk of hemolysis, which can lead to adverse outcomes and in some cases death. Accordingly, in one aspect, there is a need for a pump that can provide sufficient flow at significantly reduced rotational speeds. These and other problems are overcome by the inventions described herein.

Further, there is a need for a motor configured to drive an operative device, e.g., an impeller, at a distal portion of the pump. It can be important for the motor to be configured to allow for percutaneous insertion of the pump's operative device.

SUMMARY OF THE INVENTION

There is an urgent need for a pumping device that can be inserted percutaneously and also provide full cardiac rate flows of the left, right, or both the left and right sides of the heart when called for.

In one embodiment, a catheter pump is disclosed. The catheter pump can include a catheter assembly. The catheter assembly can include a drive shaft having a proximal end and a distal end. An impeller may be coupled with the distal end of the drive shaft. A driven magnet assembly may be coupled with the proximal end of the drive shaft. The driven magnet assembly can include a driven magnet housing having a driven magnet. The catheter pump can further include a drive system. The drive system can include a motor having an output shaft. The drive system can also include a drive magnet assembly coupled with the output shaft. The drive magnet assembly can include a drive magnet housing with a drive magnet disposed therein. A securement device can be configured to secure the driven magnet housing into engagement with the drive magnet housing during operation of the pump.

In another embodiment, a catheter pump is disclosed. The catheter pump can include a catheter assembly. The catheter assembly can comprise a drive shaft having a proximal end and a distal end. An impeller can be coupled with the distal end of the drive shaft. A rotatable magnet can be coupled with the proximal end. The rotatable magnet can be disposed in a driven magnet housing. Furthermore, the catheter pump can include a drive system comprising a plurality of motor windings configured to induce rotation of the rotatable magnet when the driven magnet housing is engaged with the drive system. A locking device can be configured to be engaged by insertion of the driven magnet housing into an opening of the drive system.

In yet another embodiment, a method is disclosed. The method can include inserting a proximal portion of a catheter assembly containing a magnet into a recess of a drive unit. The method can further include engaging a locking device to secure the proximal portion of the catheter assembly to the drive unit.

In another embodiment, a catheter assembly is disclosed. The catheter assembly can include a catheter body having a proximal portion and a distal portion. An operative device can be coupled to the distal portion of the catheter body. A tip member can be coupled to a distal portion of the operative device. The tip member can have a lumen comprising a first section and a second section connected to the first section. An inner diameter of the first section can be larger than an inner diameter of the second section.

In one embodiment, a catheter pump is provided that includes a catheter assembly and a drive system, and a securement device. The catheter assembly includes a drive shaft, an impeller, and a driven assembly. The drive shaft has a proximal end and a distal end. The impeller is coupled with the distal end of the drive shaft. The driven assembly may be coupled with the proximal end of the drive shaft, the driven assembly is disposed in a driven housing. The drive system includes a motor having an output shaft and a drive assembly coupled with the output shaft. The drive assembly includes a drive housing with at least one magnet disposed therein. The securement device is configured to prevent disengagement of the driven housing from the drive housing during operation of the pump.

In one embodiment, a catheter pump is provided that includes a catheter assembly and a drive system, and a damper. The catheter assembly includes a drive shaft, an impeller, and a driven member. The drive shaft has a proximal end and a distal end. The impeller is coupled with the distal end of the drive shaft. The driven member is coupled with the proximal end of the drive shaft. The drive system includes a motor having an output shaft and a drive member coupled with the output shaft.

In one variant, the catheter pump can have a damper disposed between the drive and driven member. The damper can be configured to isolate the drive member or the motor from vibration in the catheter assembly. The damper can be configured to suppress noise at or around the connection between the drive and drive members.

Preferably, the damper is disposed radially around the output shaft, e.g., completely surrounding the output shaft. The damper can be disposed between separable housings of the catheter assembly and drive system, e.g., abutting a distal face of a drive system housing and a proximal face of a driven member housing disposed on the proximal end of the catheter assembly.

This embodiment can be augmented in some embodiments with a disconnectable coupling between the drive and driven members. For example, a securement device can be configured to permit selective disengagement of these components from each other. The securement device can be configured to prevent disengagement of the driven housing from the drive housing during operation of the pump.

Connection of the drive and driven members can be by the mutual attraction of opposing poles of permanent magnets disposed therein. Alternatively, the driven member can be positioned to be acted upon magnetic fields generated in the winding, e.g., using commutation in the windings. In another embodiment, the drive and driven members are coupled using direct mechanical drive, such as with gears, splines or other abutting surfaces.

In another embodiment, a catheter pump is provided that has a catheter assembly, a drive system, and a locking device. The catheter assembly has a drive shaft that has a proximal end and a distal end. An impeller is coupled with the distal end of the drive shaft. A rotatable magnet is coupled with the proximal end of the drive shaft. The rotatable magnet is disposed in a driven magnet housing. The drive system has a plurality of motor windings configured to induce rotation of the rotatable magnet after the driven magnet housing is engaged with the drive system. The locking device is configured to be engaged by insertion of the driven magnet housing into a portion or recess of the drive system.

Rotation can be induced in the rotatable magnet by the mutual attraction of opposing poles of permanent magnets. The rotatable magnet can be an assembly having one or a first plurality of permanent magnets and one or a second plurality of permanent magnets can be mounted on a shaft of the motor having the motor windings. Pairing of opposite poles of two magnets or of the magnets of the first and second pluralities of permanent magnets can induce rotation that can be transferred to the drive shaft. Alternatively, the rotatable magnet can be positioned to be acted upon magnetic fields generated in the winding, e.g., using commutation in the windings.

In another embodiment, a method is provided. A proximal portion of a catheter assembly containing a magnet is inserted into a recess of a drive unit. A locking device is engaged to secure the proximal portion of the catheter assembly to a distal portion of the drive unit.

BRIEF DESCRIPTION OF THE DRAWINGS

A more complete appreciation of the subject matter of this application and the various advantages thereof can be realized by reference to the following detailed description, in which reference is made to the accompanying drawings in which:

FIG. 4 is a schematic view of a catheter assembly and a drive assembly;

FIG. 11 illustrates a side schematic view of a motor assembly according to another embodiment;

FIGS. 12A-12B illustrates side schematic views of a motor assembly according to yet another embodiment;

More detailed descriptions of various embodiments of components for heart pumps useful to treat patients experiencing cardiac stress, including acute heart failure, are set forth below.

DETAILED DESCRIPTION

Figure 1:
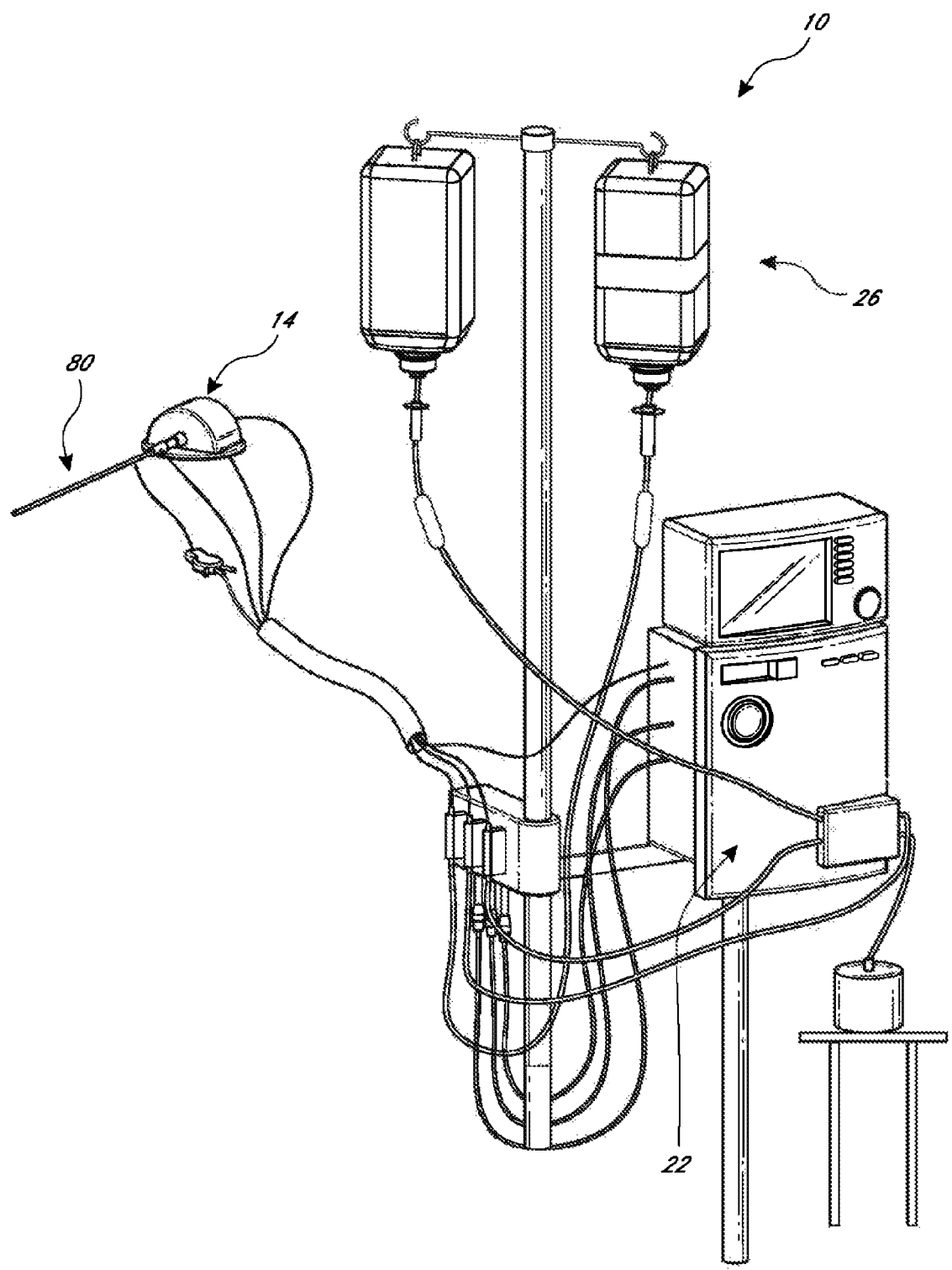
FIG. 1 illustrates one embodiment of a catheter pump configured for percutaneous application and operation.
Figure 2:
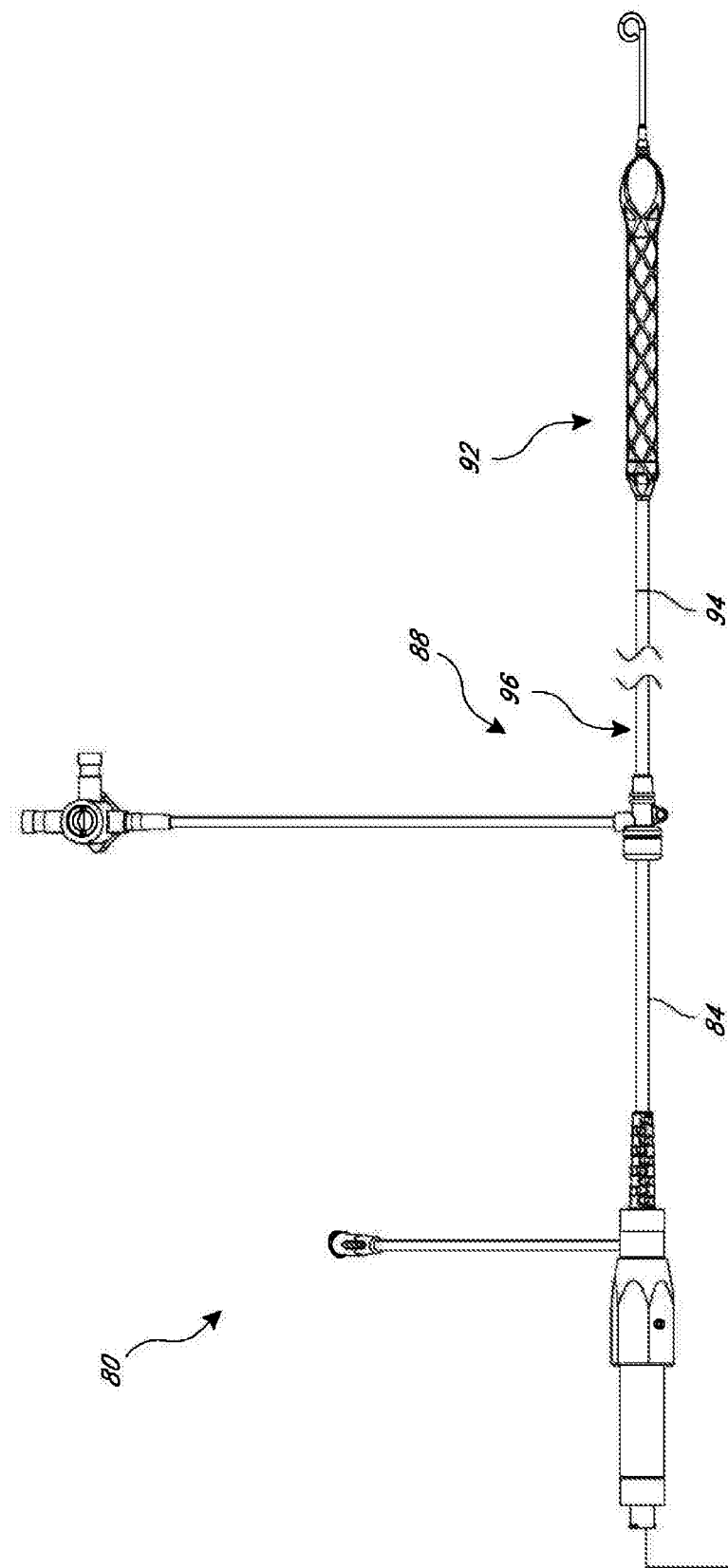
FIG. 2 is a plan view of one embodiment of a catheter adapted to be used with the catheter pump of FIG. 1.
Figure 3:
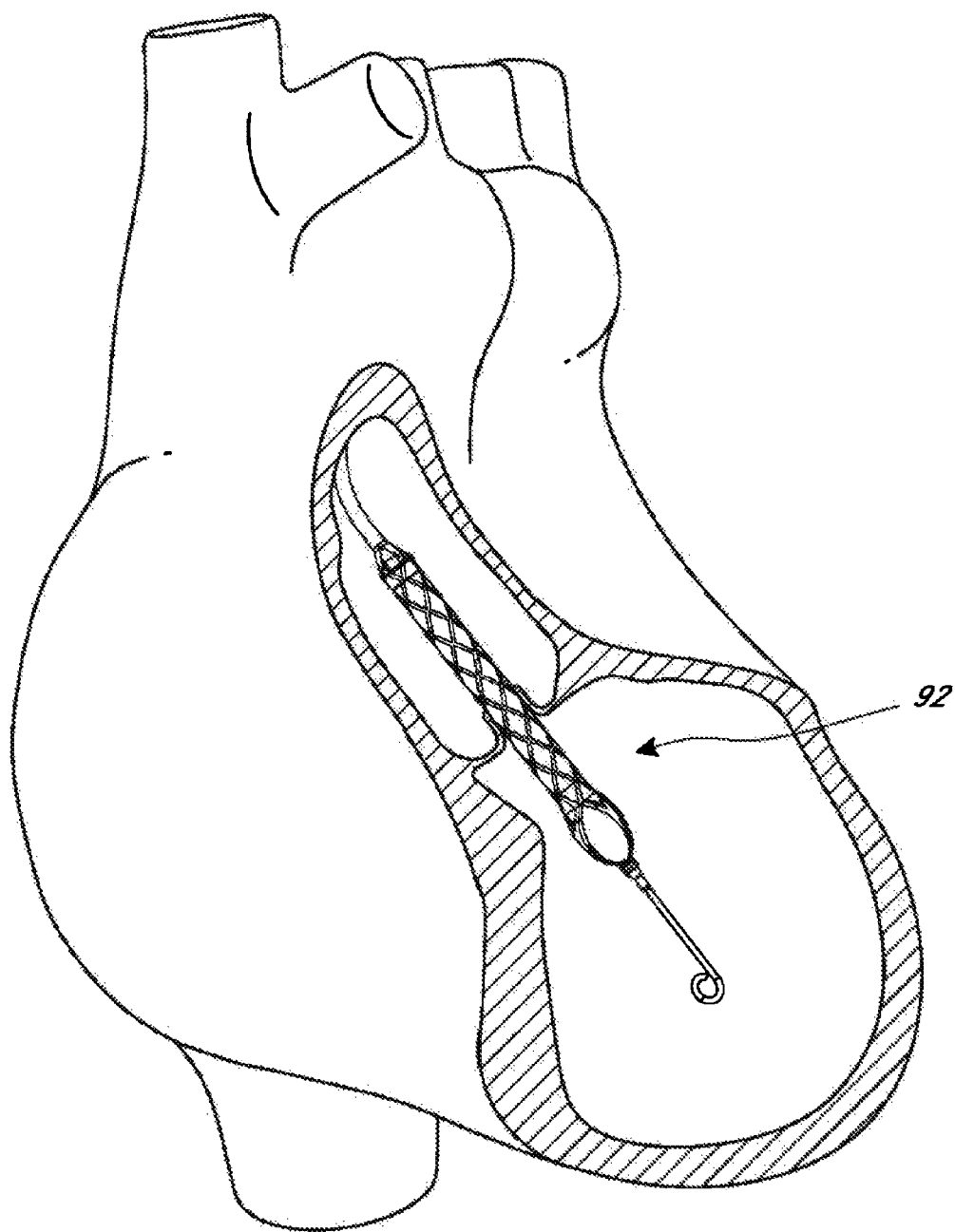
FIG. 3 show a distal portion of the catheter system similar to that of FIG. 2 in position within the anatomy.

This application is directed to apparatuses for inducing motion of a fluid relative to the apparatus. For example, an operative device, such as an impeller, can be coupled at a distal portion of the apparatus. In particular, the disclosed embodiments generally relate to various configurations for a motor adapted to drive an impeller at a distal end of a catheter pump, e.g., a percutaneous heart pump. The disclosed motor assembly may be disposed outside the patient in some embodiments. In other embodiments, the disclosed motor assembly can be miniaturized and sized to be inserted within the body. FIGS. 1-3 show aspects of a catheter pump 10 that can provide high performance flow rates. The pump 10 includes a motor driven by a controller 22. The controller 22 directs the operation of the motor 14 and an infusion system 26 that supplies a flow of infusate in the pump 10. A catheter system 80 that can be coupled with the motor 14 houses an impeller within a distal portion thereof. In various embodiments, the impeller is rotated remotely by the motor 14 when the pump 10 is operating. For example, the motor 14 can be disposed outside the patient. In some embodiments, the motor 14 is separate from the controller 22, e.g., to be placed closer to the patient. In other embodiments, the motor 14 is part of the controller 22. In still other embodiments, the motor is miniaturized to be insertable into the patient. Such embodiments allow the drive shaft to be much shorter, e.g., shorter than the distance from the aortic valve to the aortic arch (about 5 cm or less). Some examples of miniaturized motors catheter pumps and related components and methods are discussed in U.S. Pat. Nos. 5,964,694; 6,007,478; 6,178,922; and 6,176,848, all of which are hereby incorporated by reference herein in their entirety for all purposes. Various embodiments of a motor are disclosed herein, including embodiments having separate drive and driven assemblies to enable the use of a guidewire guide passing through the catheter pump. As explained herein, a guidewire guide can facilitate passing a guidewire through the catheter pump for percutaneous delivery of the pump's operative device to a patient's heart.

FIG. 3 illustrates one use of the catheter pump 10. A distal portion of the pump 10, which can include an impeller assembly 92, is placed in the left ventricle LV of the heart to pump blood from the LV into the aorta. The pump 10 can be used in this way to treat patients with a wide range of conditions, including cardiogenic shock, myocardial infarction, and other cardiac conditions, and also to support a patient during a procedure such as percutaneous coronary intervention. One convenient manner of placement of the distal portion of the pump 10 in the heart is by percutaneous access and delivery using the Seldinger technique or other methods familiar to cardiologists. These approaches enable the pump 10 to be used in emergency medicine, a catheter lab and in other non-surgical settings. Modifications can also enable the pump 10 to support the right side of the heart. Example modifications that could be used for right side support include providing delivery features and/or shaping a distal portion that is to be placed through at least one heart valve from the venous side, such as is discussed in U.S. Pat. Nos. 6,544,216; 7,070,555; and US 2012-0203056A1, all of which are hereby incorporated by reference herein in their entirety for all purposes.

FIG. 2 shows features that facilitate small blood vessel percutaneous delivery and high performance, including up to and in some cases exceeding normal cardiac output in all phases of the cardiac cycle. In particular, the catheter system 80 includes a catheter body 84 and a sheath assembly 88. The impeller assembly 92 is coupled with the distal end of the catheter body 84. The impeller assembly 92 is expandable and collapsible. In the collapsed state, the distal end of the catheter system 80 can be advanced to the heart, for example, through an artery. In the expanded state the impeller assembly 92 is able to pump blood at high flow rates. FIGS. 2 and 3 illustrate the expanded state. The collapsed state can be provided by advancing a distal end 94 of an elongate body 96 distally over the impeller assembly 92 to cause the impeller assembly 92 to collapse. This provides an outer profile throughout the catheter assembly 80 that is of small diameter, for example, to a catheter size of about 12.5 FR in various arrangements.

In some embodiments, the impeller assembly 92 includes a self-expanding material that facilitates expansion. The catheter body 84 on the other hand preferably is a polymeric body that has high flexibility. When the impeller assembly 92 is collapsed, as discussed above, high forces are applied to the impeller assembly 92. These forces are concentrated at a connection zone, where the impeller assembly 92 and the catheter body 84 are coupled together. These high forces, if not carefully managed can result in damage to the catheter assembly 80 and in some cases render the impeller within the impeller assembly 92 inoperable. Robust mechanical interface, are provided to assure high performance.

The mechanical components rotatably supporting the impeller within the impeller assembly 92 permit high rotational speeds while controlling heat and particle generation that can come with high speeds. The infusion system 26 delivers a cooling and lubricating solution to the distal portion of the catheter system 80 for these purposes. However, the space for delivery of this fluid is extremely limited. Some of the space is also used for return of the infusate. Providing secure connection and reliable routing of infusate into and out of the catheter assembly 80 is critical and challenging in view of the small profile of the catheter body 84.

When activated, the catheter pump system can effectively increase the flow of blood out of the heart and through the patient's vascular system. In various embodiments disclosed herein, the pump can be configured to produce a maximum flow rate (e.g. low mm Hg) of greater than 4 Lpm, greater than 4.5 Lpm, greater than 5 Lpm, greater than 5.5 Lpm, greater than 6 Lpm, greater than 6.5 Lpm, greater than 7 Lpm, greater than 7.5 Lpm, greater than 8 Lpm, greater than 9 Lpm, or greater than 10 Lpm. In various embodiments, the pump can be configured to produce an average flow rate at 62 mmHg of greater than 2 Lpm, greater than 2.5 Lpm, greater than 3 Lpm, greater than 3.5 Lpm, greater than 4 Lpm, greater than 4.25 Lpm, greater than 4.5 Lpm, greater than 5 Lpm, greater than 5.5 Lpm, or greater than 6 Lpm.

Various aspects of the pump and associated components are similar to those disclosed in U.S. Pat. Nos. 7,393,181; 8,376,707; 7,841,976; 7,022,100; and 7,998,054, and in U.S. Pub. Nos. 2011/0004046; 2012/0178986; 2012/0172655; 2012/0178985; and 2012/0004495, the entire contents of each of which are incorporated herein for all purposes by reference. In addition, this application incorporates by reference in its entirety and for all purposes the subject matter disclosed in each of the following concurrently filed applications: application Ser. No. 13/802,556, entitled "DISTAL BEARING SUPPORT," filed on the same date as this application; Application No. 61/780,656, entitled "FLUID HANDLING SYSTEM," filed on the same date as this application; application Ser. No. 13/801,833, entitled "SHEATH SYSTEM FOR CATHETER PUMP," filed on the same date as this application; application Ser. No. 13/802, 570, entitled "IMPELLER FOR CATHETER PUMP," filed on the same date as this application; and application Ser. No. 13/801,528, entitled "CATHETER PUMP," filed on the same date as this application.

Another example of a catheter assembly 100A is illustrated in FIG. 4. Embodiments of the catheter pump of this application can be configured with a motor that is capable of coupling to (and in some arrangements optionally decoupling from) the catheter assembly 100A. This arrangement provides a number of advantages over a non-disconnectable housing. For example, access can be provided to a proximal end of the catheter assembly 100A prior to or during use. In one configuration, a catheter pump is delivered over a guidewire. The guidewire may be conveniently extended through the entire length of the catheter assembly 100A and out of a proximal portion thereof that is completely enclosed in a coupled configuration. For this approach, connection of the proximal portion of the catheter assembly 100A to a motor housing can be completed after a guidewire has been used to guide the operative device of the catheter pump to a desired location within the patient, e.g., to a chamber of the patient's heart. In one embodiment, the connection between the motor housing and the catheter assembly is configured to be permanent, such that the catheter assembly, the motor housing and the motor are disposable components. However, in other implementations, the coupling between the motor housing and the catheter assembly is disengageable, such that the motor and motor housing can be decoupled from the catheter assembly after use. In such embodiments, the catheter assembly distal of the motor can be disposable, and the motor and motor housing can be re-usable.

Moving from the distal end of the catheter assembly 100A of FIG. 4 to the proximal end, a priming apparatus 1400 can be disposed over an impeller assembly 116A. As explained above, the impeller assembly 116A can include an expandable cannula or housing and an impeller with one or more blades. As the impeller rotates, blood can be pumped proximally (or distally in some implementations) to function as a cardiac assist device.

Figure 4A:
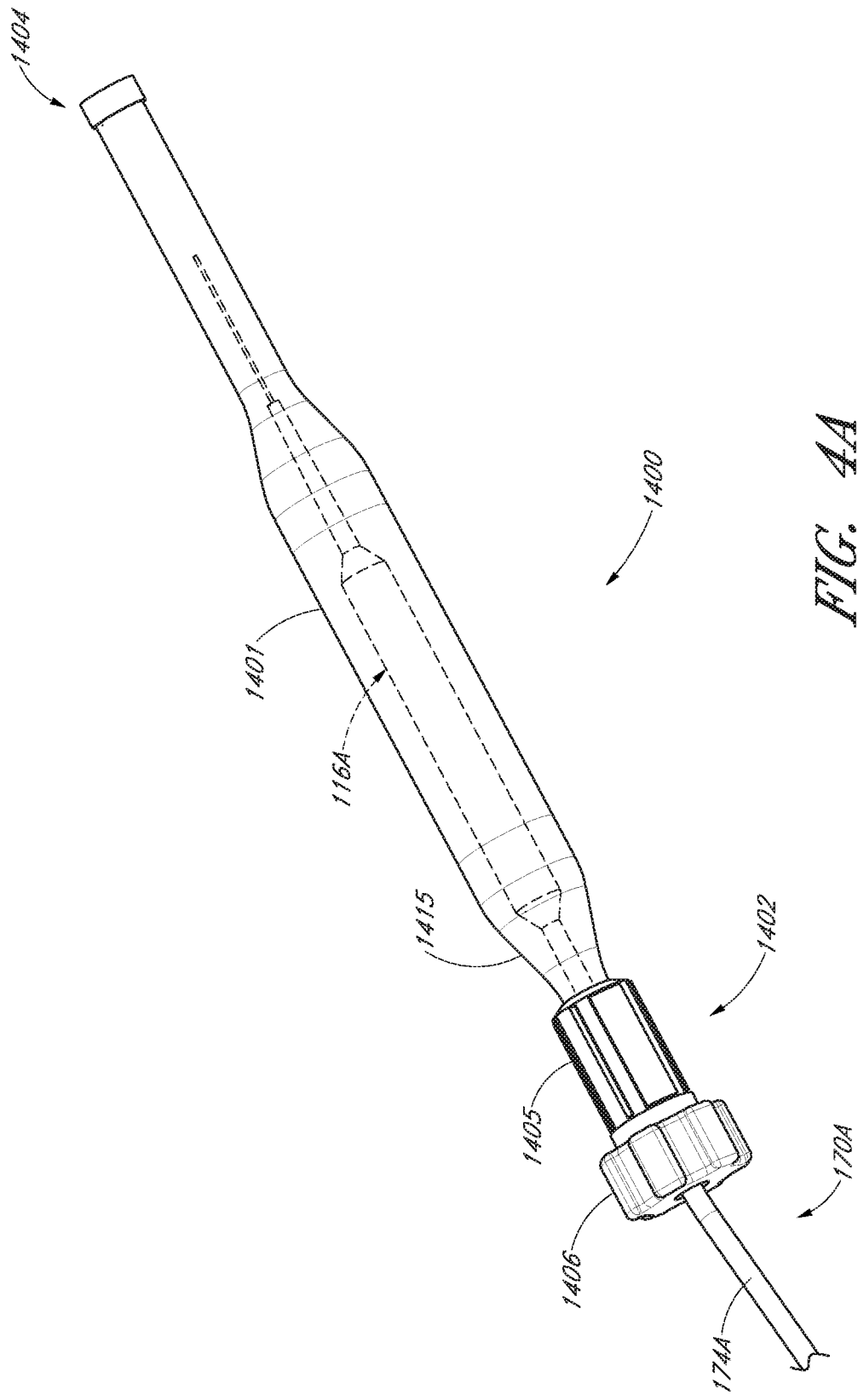
FIG. 4A is an enlarged view of a priming apparatus shown in FIG. 4.

FIG. 4 also shows one example of a priming apparatus 1400 disposed over the impeller assembly 116A near the distal end 170A of the elongate body 174A. FIG. 4A is an enlarged view of the priming apparatus 1400 shown in FIG. 4. The priming apparatus 1400 can be used in connection with a procedure to expel air from the impeller assembly 116A, e.g., any air that is trapped within the housing or that remains within the elongate body 174A near the distal end 170A. For example, the priming procedure may be performed before the pump is inserted into the patient's vascular system, so that air bubbles are not allowed to enter and/or injure the patient. The priming apparatus 1400 can include a primer housing 1401 configured to be disposed around both the elongate body 174A and the impeller assembly 116A. A sealing cap 1406 can be applied to the proximal end 1402 of the primer housing 1401 to substantially seal the priming apparatus 1400 for priming, i.e., so that air does not proximally enter the elongate body 174A and also so that priming fluid does not flow out of the proximal end of the housing 1401. The sealing cap 1406 can couple to the primer housing 1401 in any way known to a skilled artisan. However, in some embodiments, the sealing cap 1406 is threaded onto the primer housing by way of a threaded connector 1405 located at the proximal end 1402 of the primer housing 1401. The sealing cap 1406 can include a sealing recess disposed at the distal end of the sealing cap 1406. The sealing recess can be configured to allow the elongate body 174A to pass through the sealing cap 1406.

The priming operation can proceed by introducing fluid into the sealed priming apparatus 1400 to expel air from the impeller assembly 116A and the elongate body 174A. Fluid can be introduced into the priming apparatus 1400 in a variety of ways. For example, fluid can be introduced distally through the elongate body 174A into the priming apparatus 1400. In other embodiments, an inlet, such as a luer, can optionally be formed on a side of the primer housing 1401 to allow for introduction of fluid into the priming apparatus 1400.

A gas permeable membrane can be disposed on a distal end 1404 of the primer housing 1401. The gas permeable membrane can permit air to escape from the primer housing 1401 during priming.

The priming apparatus 1400 also can advantageously be configured to collapse an expandable portion of the catheter assembly 100A. The primer housing 1401 can include a funnel 1415 where the inner diameter of the housing decreases from distal to proximal. The funnel may be gently curved such that relative proximal movement of the impeller housing causes the impeller housing to be collapsed by the funnel 1415. During or after the impeller housing has been fully collapsed, the distal end 170A of the elongate body 174A can be moved distally relative to the collapsed housing. After the impeller housing is fully collapsed and retracted into the elongate body 174A of the sheath assembly, the catheter assembly 100A can be removed from the priming housing 1400 before a percutaneous heart procedure is performed, e.g., before the pump is activated to pump blood. The embodiments disclosed herein may be implemented such that the total time for infusing the system is minimized or reduced. For example, in some implementations, the time to fully infuse the system can be about six minutes or less. In other implementations, the time to infuse can be about three minutes or less. In yet other implementations, the total time to infuse the system can be about 45 seconds or less. It should be appreciated that lower times to infuse can be advantageous for use with cardiovascular patients.

With continued reference to FIG. 4, the elongate body 174A extends proximally from the impeller assembly 116A to an infusate device 195 configured to allow for infusate to enter the catheter assembly 100A and for waste fluid to leave the catheter assembly 100A. A catheter body 120A (which also passes through the elongate body 174A) can extend proximally and couple to a driven assembly 201. The driven assembly 201 can be configured to receive torque applied by a drive assembly 203, which is shown as being decoupled from the driven assembly 201 and the catheter assembly 100A in FIG. 4. Although not shown in FIG. 4, a drive shaft can extend from the driven assembly 201 through the catheter body 120A to couple to an impeller shaft at or proximal to the impeller assembly 116A. The catheter body 120A can pass within the elongate catheter body 174A such that the external catheter body 174A can axially translate relative to the catheter body 120A.

In addition, FIG. 4 illustrates a guidewire 235 extending from a proximal guidewire opening 237 in the driven assembly 201. Before inserting the catheter assembly 100A into a patient, a clinician may insert the guidewire 235 through the patient's vascular system to the heart to prepare a path for the operative device (e.g., the impeller assembly 116A) to the heart. In some embodiments, the catheter assembly can include a guidewire guide tube (see FIG. 12) passing through a central internal lumen of the catheter assembly 100A from the proximal guidewire opening 237. The guidewire guide tube can be pre-installed in the catheter assembly 100A to provide the clinician with a preformed pathway along which to insert the guidewire 235.

In one approach, a guidewire is first placed in a conventional way, e.g., through a needle into a peripheral blood vessel, and along the path between that blood vessel and the heart and into a heart chamber, e.g., into the left ventricle. Thereafter, a distal end opening of the catheter assembly or guidewire guide can be advanced over the proximal end of the guidewire 235 to enable delivery to the catheter assembly 100A. After the proximal end of the guidewire 235 is urged proximally within the catheter assembly 100A and emerges from the guidewire opening 237 and/or guidewire guide, the catheter assembly 100A can be advanced into the patient. In one method, the guidewire guide is withdrawn proximally while holding the catheter assembly 100A. The guidewire guide is taken off of the catheter assembly 100A so that guidewire lumens from the proximal end to the distal end of the catheter assembly 100A are directly over the guidewire.

Alternatively, the clinician can thus insert the guidewire 235 through the proximal guidewire opening 237 and urge the guidewire 235 along the guidewire guide tube until the guidewire 235 extends from a distal guidewire opening (not shown) in the distal end of the catheter assembly 100A. The clinician can continue urging the guidewire 235 through the patient's vascular system until the distal end of the guidewire 235 is positioned in the desired chamber of the patient's heart. As shown in FIG. 4, a proximal end portion of the guidewire 235 can extend from the proximal guidewire opening 237. Once the distal end of the guidewire 235 is positioned in the heart, the clinician can maneuver the impeller assembly 116A over the guidewire 235 until the impeller assembly 116A reaches the distal end of the guidewire 235 in the heart. The clinician can remove the guidewire 235 and the guidewire guide tube. The guidewire guide tube can also be removed before or after the guidewire 235 is removed in some implementations.

After removing at least the guidewire 235, the clinician can activate a motor to rotate the impeller and begin operation of the pump.

One problem that arises when using the guidewire 235 to guide the operative device to the heart is that a central lumen or tube (e.g., a guidewire guide) is typically formed to provide a path for the guidewire 235. In some implementations, it may be inconvenient or inoperable to provide a motor or drive assembly having a lumen through which the guidewire 235 can pass. Moreover, in some implementations, it may be desirable to provide the motor or drive assembly separate from the catheter assembly 100A, e.g., for manufacturing or economic purposes. Thus, it can be advantageous to provide a means to couple the drive assembly 203 to the driven assembly 201, while enabling the use of a guidewire guide through which a guidewire may be passed. Preferably, the drive assembly 203 can be securely coupled to the driven assembly 201 such that vibratory, axial, or other external forces do not decouple the drive assembly 203 from the driven assembly 201 during operation. Moreover, the coupling should preferably allow a motor to operate effectively so that the drive shaft is rotated at the desired speed and with the desired torque.

Figure 5:
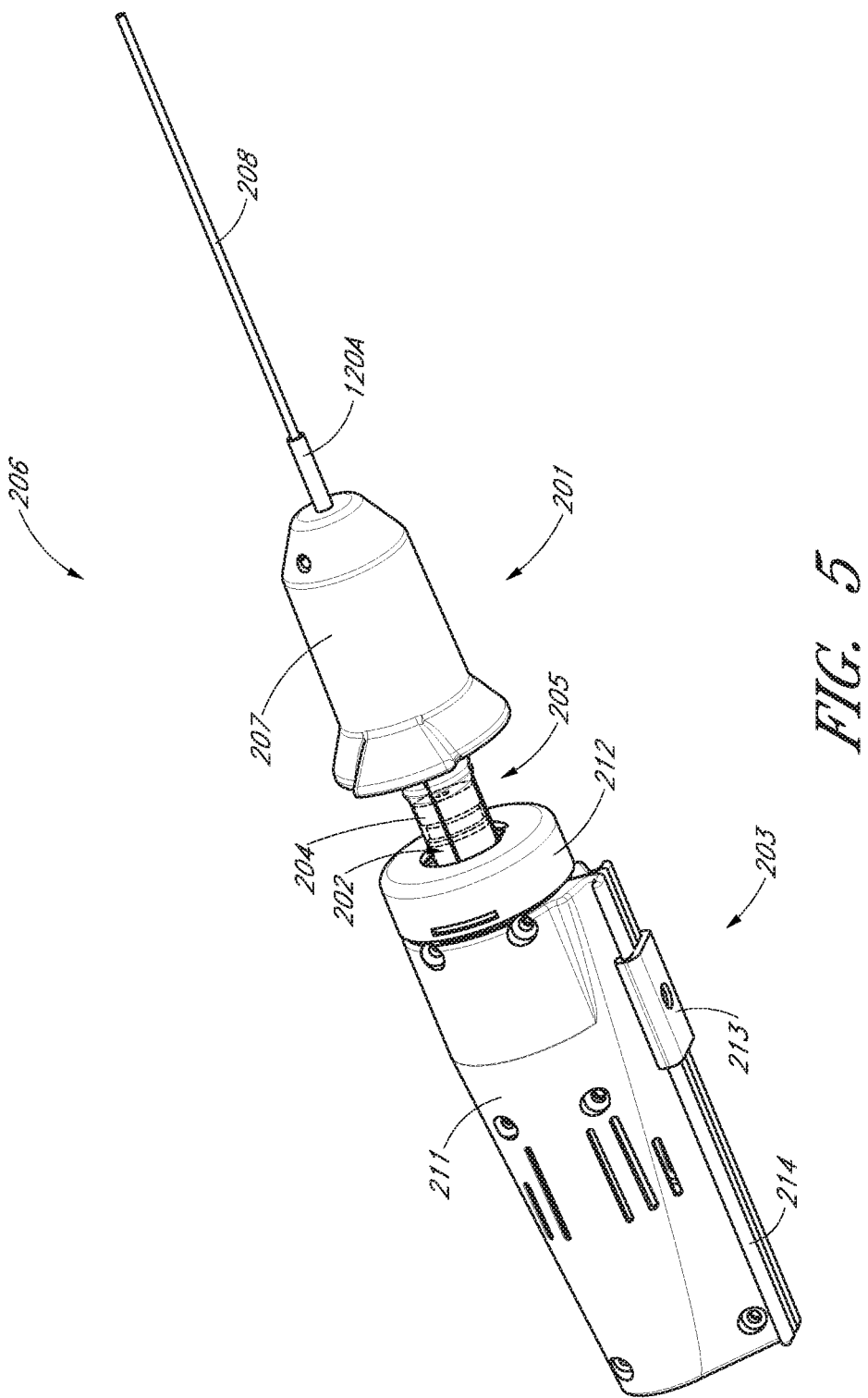
FIG. 5 is a three dimensional (3D) perspective view of a motor assembly as the drive assembly is being coupled to a driven assembly.

FIG. 5 illustrates one embodiment of a motor assembly 206 as the driven assembly 201 is being coupled to the drive assembly 203. The driven assembly 201 can include a flow diverter 205 and a flow diverter housing 207 that houses the flow diverter 205. The flow diverter 205 can be configured with a plurality of internal cavities, passages, and channels that are configured to route fluid to and from the patient during a medical procedure. As discussed below, an infusate can be directed into the flow diverter from a source of infusate. The infusate is a fluid that flows into the catheter body 120A to provide useful benefits, such as cooling moving parts and keeping blood from entering certain parts of the catheter assembly 100A. The infusate is diverted distally by flow channels in the flow diverter 205. Some of the infusate that flows distally is re-routed back through the catheter body 120A and may be diverted out of the catheter assembly 100A by the flow diverter 205. Moreover, a driven magnet 204 can be disposed within the flow diverter 205 in various embodiments. For example, the driven magnet 204 can be journaled for rotation in a proximal portion of the flow diverter housing 207. The proximal portion can project proximally of a proximal face of a distal portion of the flow diverter housing 207. In other embodiments, the driven magnet 204 can be disposed outside the flow diverter 205. The driven magnet 204 can be configured to rotate freely relative to the flow diverter 205 and/or the flow diverter housing 207. The catheter body 120A can extend from a distal end of the flow diverter housing 207. Further, a drive shaft 208 can pass through the catheter body 120A from the proximal end of the flow diverter housing 207 to the distal end 170A of the elongate body 174A. The drive shaft 208 can be configured to drive the impeller located at the distal end of the catheter assembly 100A. In some embodiments, a distal end of the drive shaft 208 can couple to an impeller shaft, which rotates the impeller.

The drive assembly 203 can include a drive housing or a motor housing 211 having an opening 202 in a cap 212 of the motor housing 211. The motor housing 211 can also have a sliding member 213, which can be configured to couple to the patient's body by way of, e.g., a connector 291 coupled to an adhesive or bandage on the patient's body. Because the motor and motor housing 211 can have a relatively high mass, it can be important to ensure that the motor housing 211 is stably supported. In one implementation, therefore, the motor housing 211 can be supported by the patient's body by way of the sliding member 213 and the connector 291 shown in FIG. 4. The sliding member 213 can slide along a track 214 located on a portion of the motor housing 211, such that relative motion between the motor assembly 206 and the patient does not decouple the sliding member 213 from the patient's body. The sliding member 213 and connector 291 can therefore be configured to provide a structural interface between the motor housing 206 and a platform for supporting the motor housing 211. As explained above, in some arrangements, the platform supporting the motor housing 211 can be the patient, since the motor housing 211 may be positioned quite close to the insertion point. In other arrangements, however, the platform supporting the motor housing 211 may be an external structure.

To couple the drive assembly 203 to the driven assembly 201, the clinician or user can insert the proximal portion of the flow diverter 205 into the opening 202 in the cap 212 of the motor housing 212. After passing through the opening 202, the proximal portion of the flow diverter can reside within a recess formed within the motor housing 211. In some implementations, a securement device is configured to lock or secure the drive assembly 203 to the driven assembly 201 once the driven assembly 201 is fully inserted into the drive assembly 203. In other implementations, the securement device can be configured to secure the drive assembly 203 to the driven assembly 201 by inserting the driven assembly 201 into the drive assembly 203 and then rotating the drive assembly 203 with respect to the driven assembly. In some implementations, coupling the drive assembly 203 to the driven assembly 201 may be irreversible, such that there may be no release mechanism to decouple the drive assembly 203 from the driven assembly 201. In implementations without a release mechanism, the catheter assembly 100A (including the driven assembly 201) and the motor housing 211 may be disposable components. In other implementations, however, a release mechanism may be provided to remove the drive assembly 203 from the driven assembly 201. The drive assembly 203 can thereby be used multiple times in some embodiments.

Figure 6:
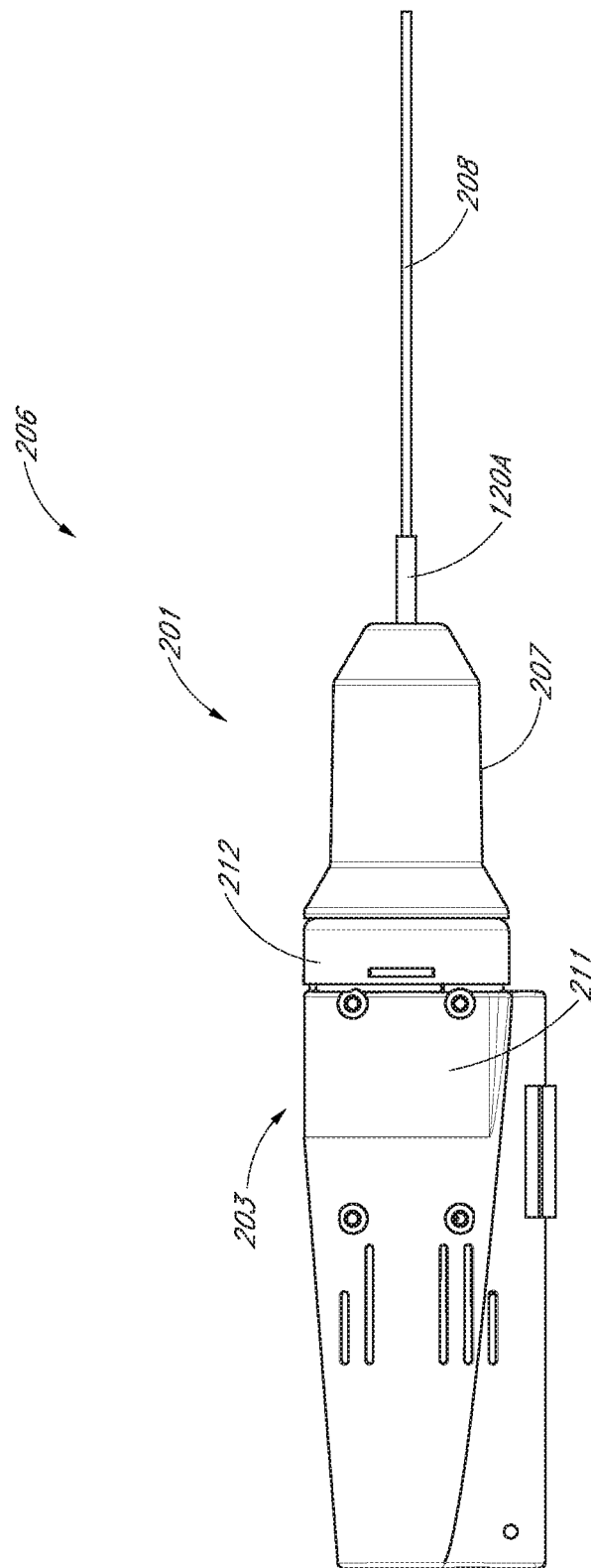
FIG. 6 is a 3D perspective view of the motor assembly once the drive assembly has been coupled and secured to the driven assembly.

FIG. 6 illustrates the motor assembly 206 in the assembled state, e.g., after the drive assembly 203 has been secured to the driven assembly 201. When the drive assembly 203 is activated (e.g., a motor is activated to rotate an output shaft), the driven assembly 201, which is operably coupled to the drive assembly, is also activated. The activated driven assembly can cause the drive shaft 208 to rotate, which in turn causes the impeller to rotate to thereby pump blood through the patient.

Figure 7:
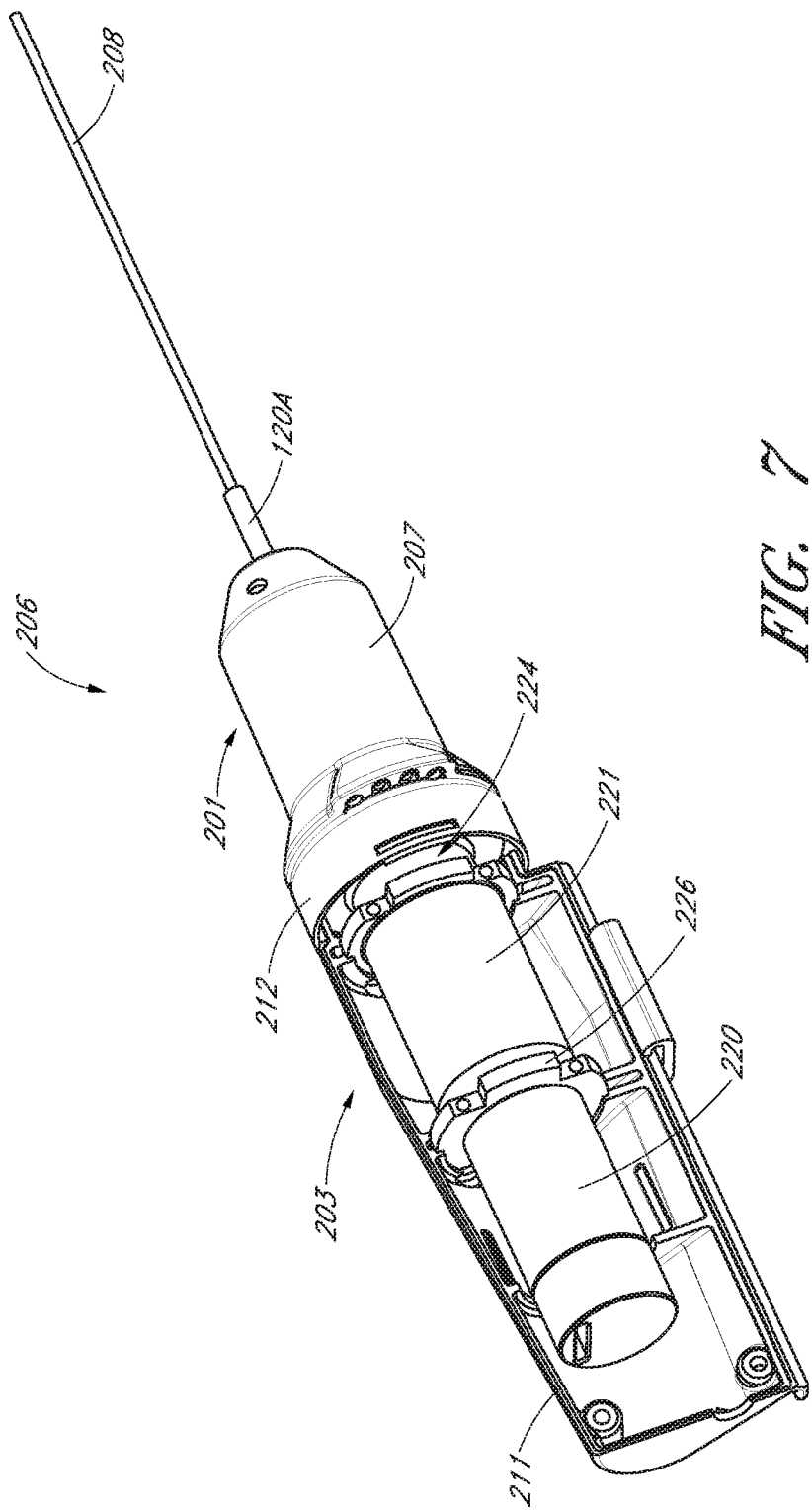
FIG. 7 is a 3D perspective view of the motor assembly of FIG. 6, wherein various components have been removed for ease of illustration.
Figure 8:
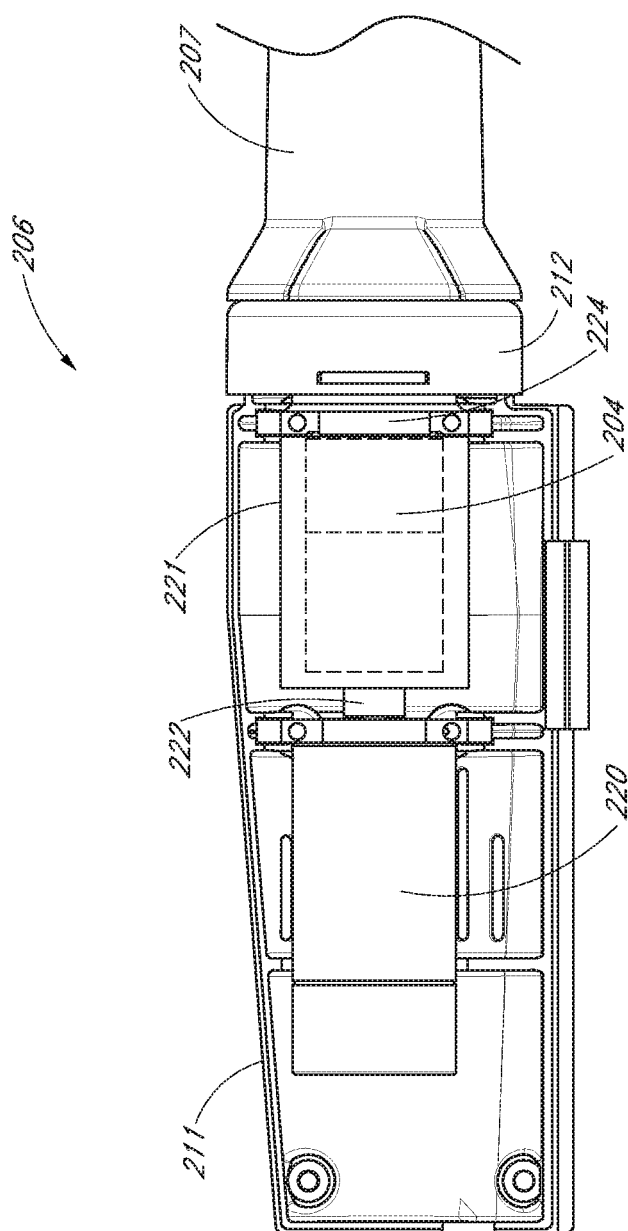
FIG. 8 is a plan view of the motor assembly that illustrates a motor, a drive magnet and a driven magnet.

FIGS. 7-8 illustrate the motor assembly 206 with one wall of the motor housing 211 removed so that various internal components in the housing 211 can be better illustrated. A motor 220 can be positioned within the housing 211 and mounted by way of a motor mount 226. The motor 220 can operably couple to a drive magnet 221. For example, the motor 220 can include an output shaft 222 that rotates the drive magnet 221. In some implementations, the drive magnet 221 can rotate relative to the motor mount 226 and the motor housing 211. Further, in some arrangements, the drive magnet 221 can be free to translate axially between the motor mount and a barrier 224. One advantage of the translating capability is to enable the drive magnet 221 and the driven magnet 204 to self-align by way of axial translation. The barrier 224 can be mounted to the motor housing 211 and at least partially within the cap 212 to support at least the drive magnet 221. In other implementations, the drive assembly 203 can comprise a plurality of motor windings configured to induce rotation of the drive magnet 221. In still other embodiments, motor windings can operate directly on a driven magnet within the driven assembly 201. For example, the windings can be activated in phases to create an electric field and thereby commutate the driven magnet.

In FIG. 8, the drive magnet 221 is illustrated in phantom, such that the driven magnet 204 can be seen disposed within the drive magnet 221. Although not illustrated, the poles of the drive magnet 221 can be formed on an interior surface of the drive magnet 221, and the poles of the driven magnet 204 can be formed on an exterior surface of the driven magnet 204. As the drive magnet 221 rotates, the poles of the drive magnet 221 can magnetically engage with corresponding, opposite poles of the driven magnet 204 to cause the driven magnet 204 to rotate with, or follow, the drive magnet 221. Because the driven magnet 204 can be mechanically coupled to the drive shaft 208, rotation of the drive magnet 221 can cause the driven magnet 204 and the drive shaft 208 to rotate at a speed determined in part by the speed of the motor 220. Furthermore, when the driven magnet 204 is inserted into the drive magnet 221, the poles of each magnet can cause the drive magnet 221 and the driven magnet 204 to self-align. The magnetic forces between the drive magnet 221 and the driven magnet 204 can assist in coupling the drive assembly 203 to the driven assembly 201.

Figure 9:
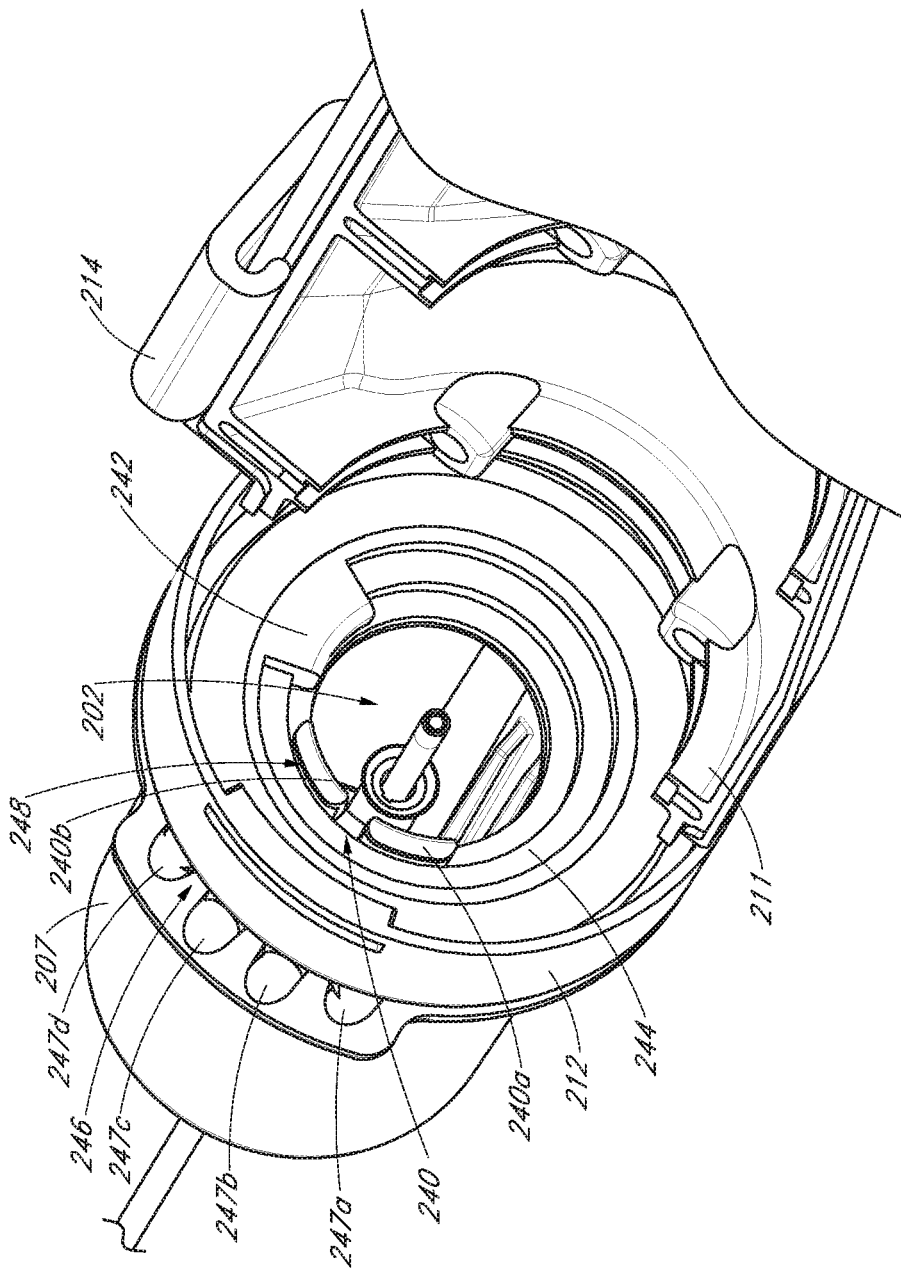
FIG. 9 is a 3D perspective view of a first securement device configured to secure the drive assembly to the driven assembly.

Turning to FIG. 9, a 3D perspective view of various components at the interface between the drive assembly 203 and the driven assembly 201 is shown. Various components have been hidden to facilitate illustration of one means to secure the drive assembly 203 to the driven assembly 201. A first securement device 240 is illustrated in FIG. 9. The first securement device can comprise a first projection 240a and a second projection 240b. Furthermore, a locking recess 244 can be formed in the cap 212 around at least a portion of a perimeter of the opening 202. A lip 242 can also extend from the perimeter at least partially into the opening 202. As shown, the lip 242 can also extend proximally from the locking recess 244 such that a step is formed between the locking recess 244 and the lip 242. Further, a flange 246 can be coupled to or formed integrally with the flow diverter housing 207. The flange 246 can include a plurality of apertures 247a, 247b, 247c, 247d that are configured to permit tubes and cables to pass therethrough to fluidly communicate with lumens within the flow diverter 205. In some implementations, three tubes and one electrical cable can pass through the apertures 247a-d. For example, the electrical cable can be configured to electrically couple to a sensor within the catheter assembly 100A, e.g., a pressure sensor. The three tubes can be configured to carry fluid to and from the catheter assembly 100A. For example, a first tube can be configured to carry infusate into the catheter assembly 100A, a second tube can be configured to transport fluids to the pressure sensor region, and the third tube can be configured to transport waste fluid out of the catheter assembly 100A. Although not illustrated, the tubes and cable(s) can pass through the apertures 247a-d of the flange 246 and can rest against the motor housing 211. By organizing the routing of the tubes and cable(s), the apertures 247a-d can advantageously prevent the tubes and cable(s) from becoming entangled with one another or with other components of the catheter pump system.

When the driven assembly 201 is inserted into the opening 202, the first and second projections 240a, 240b can pass through the opening and engage the locking recess 244. In some implementations, the projections 240a, 240b and the locking recess 244 can be sized and shaped such that axial translation of the projections 240a, 240b through the opening 202 causes a flange or tab 248 at a distal end of each projection 240a, 240b to extend over the locking recess 244. Thus, in some embodiments, once the projections 240a, 240b are inserted through the opening 202, the tabs 248 at the distal end of the projections 240a, 240b are biased to deform radially outward to engage the locking recess 244 to secure the driven assembly 201 to the drive assembly 203.

Once the driven assembly 201 is secured to the drive assembly 203, the flow diverter housing 207 can be rotated relative to the motor cap 212. By permitting relative rotation between the driven assembly 201 and the drive assembly 203, the clinician is able to position the impeller assembly 116A within the patient at a desired angle or configuration to achieve the best pumping performance. As shown in FIG. 9, however, the lip 242 can act to restrict the relative rotation between the driven assembly 201 (e.g., the flow diverter housing 207) and the drive assembly 203 (e.g. the cap 212 and the motor housing 211). As illustrated, the flange 246 and apertures 247a-d can be circumferentially aligned with the projections 240a, 240b. Further, the lip 242 can be circumferentially aligned with the sliding member 213, the track 214, and the connector 291 of the motor housing 211. If the flange 246 and projections 240a, 240b are rotated such that they circumferentially align with the lip 242, then the tubes and cable(s) that extend from the apertures 247a-d may become entangled with or otherwise obstructed by the sliding member 213 and the connector 291. Thus, it can be advantageous to ensure that the sliding member 213 and the connector 291 (or any other components on the outer surface of the housing 211) do not interfere or obstruct the tubes and cable(s) extending out of the apertures 247a-d of the flange 246. The lip 242 formed in the cap 212 can act to solve this problem by ensuring that the flange 246 is circumferentially offset from the sliding member 213 and the connector 291. For example, the flow diverter housing 207 can be rotated until one of the projections 240a, 240b bears against a side of the lip 242. By preventing further rotation beyond the side of the lip 242, the lip 242 can ensure that the flange 246 and apertures 247a-d are circumferentially offset from the sliding member 213, the track 214, and the connector 291.

In one embodiment, once the catheter assembly 100A is secured to the motor housing 211, the connection between the driven assembly 201 and the drive assembly 203 may be configured such that the drive assembly 203 may not be removed from the driven assembly 201. The secure connection between the two assemblies can advantageously ensure that the motor housing 211 is not accidentally disengaged from the catheter assembly 100A during a medical procedure. In such embodiments, both the catheter assembly 100A and the drive assembly 203 may preferably be disposable.

In other embodiments, however, it may be desirable to utilize a re-usable drive assembly 203. In such embodiments, therefore, the drive assembly 203 may be removably engaged with the catheter assembly 100A (e.g., engaged with the driven assembly 201). For example, the lip 242 may be sized and shaped such that when the drive assembly 203 is rotated relative to the driven assembly 201, the tabs 248 are deflected radially inward over the lip 242 such that the driven assembly 201 can be withdrawn from the opening 202. For example, the lip 242 may include a ramped portion along the sides of the lip 242 to urge the projections 240a, 240b radially inward. It should be appreciated that other release mechanisms are possible.

Figure 10A:
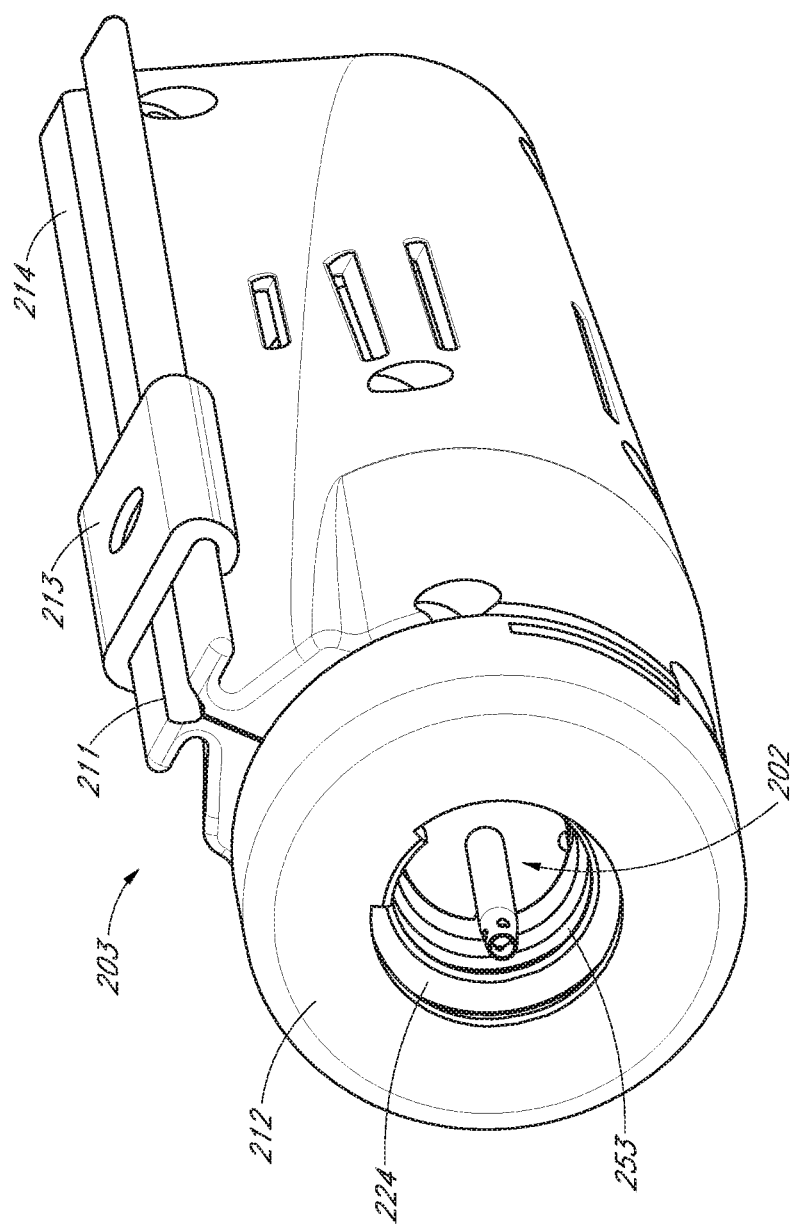
FIGS. 10A-10C are 3D perspective views of a second securement device configured to secure the drive assembly to the driven assembly.
Figure 10B:
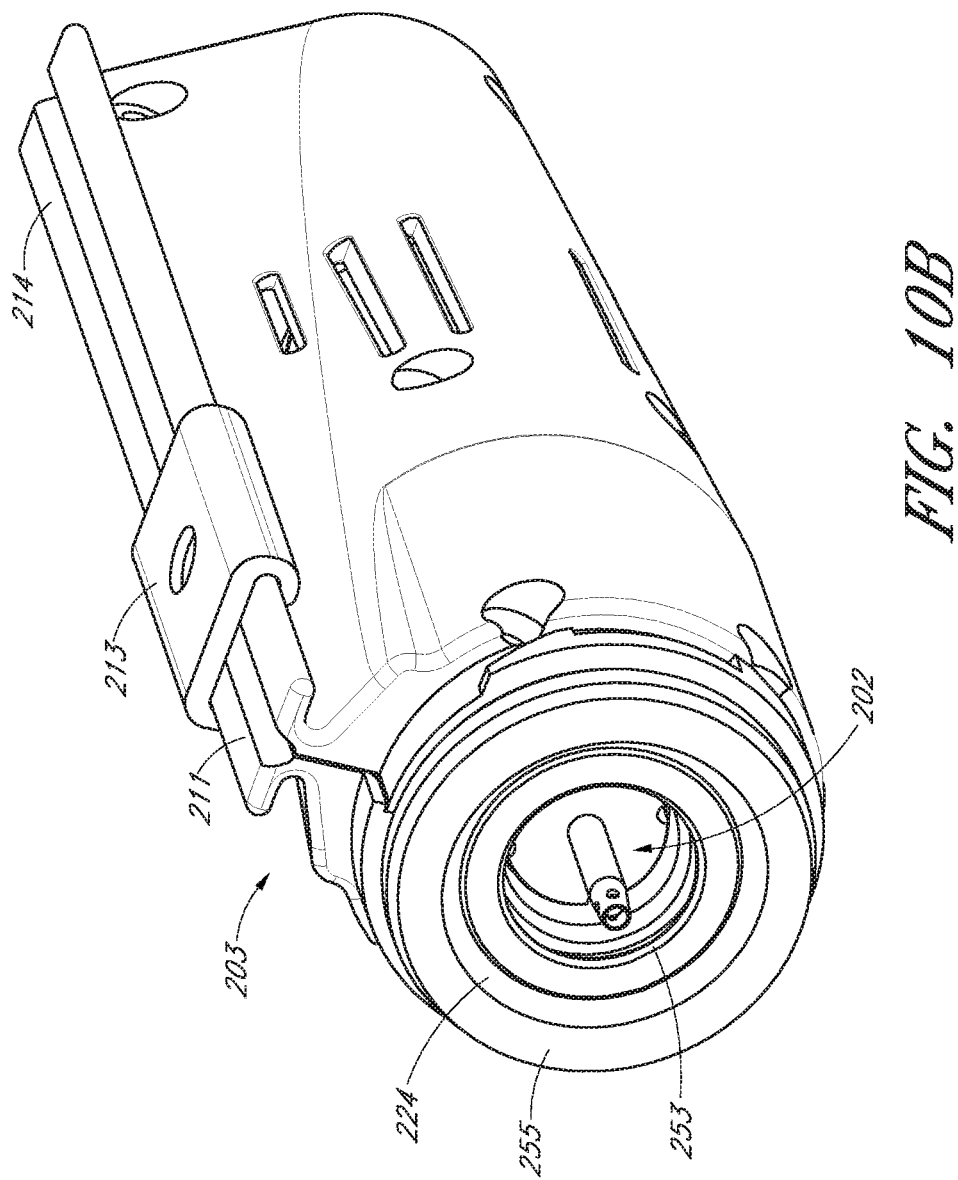
Figure 10C:
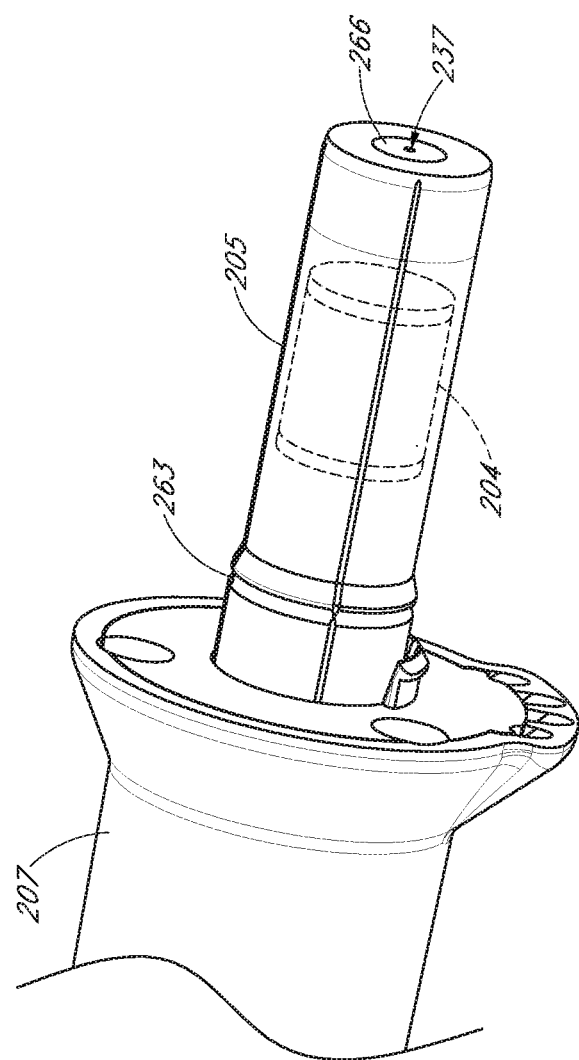

Turning to FIGS. 10A-10C, an additional means to secure the drive assembly 203 to the driven assembly 201 is disclosed. As shown in the 3D perspective view of FIG. 10A, a locking O-ring 253 can be mounted to the barrier 224 that is disposed within the motor housing 211 and at least partially within the cap 212. In particular, the locking O-ring 253 can be mounted on an inner surface of the drive or motor housing 203 surrounding the recess or opening 202 into which the driven assembly 212 can be received As explained below, the locking O-ring can act as a detent mechanism and can be configured to be secured within an arcuate channel formed in an outer surface of the driven assembly 201, e.g., in an outer surface of the flow diverter 205 in some embodiments. In other embodiments, various other mechanisms can act as a detent to secure the driven assembly 201 to the drive assembly 203. For example, in one embodiment, a spring plunger or other type of spring-loaded feature may be cut or molded into the barrier 224, in a manner similar to the locking O-ring 253 of FIGS. 10A-10C. The spring plunger or spring-loaded feature can be configured to engage the arcuate channel, as explained below with respect to FIG. 10C. Skilled artisans will understand that other types of detent mechanisms can be employed.

FIG. 10B illustrates the same 3D perspective of the drive assembly 203 as shown in FIG. 10A, except the cap 212 has been hidden to better illustrate the locking O-ring 253 and a second, stabilizing O-ring 255. The O-ring 255 is an example of a damper that can be provided between the motor 220 and the catheter assembly 100A. The damper can provide a vibration absorbing benefit in some embodiments. In other embodiment, the damper may reduce noise when the pump is operating. The damper can also both absorb vibration and reduce noise in some embodiments. The stabilizing O-ring 255 can be disposed within the cap 212 and can be sized and shaped to fit along the inner recess forming the inner perimeter of the cap 212. The stabilizing O-ring 255 can be configured to stabilize the cap 212 and the motor housing 211 against vibrations induced by operation of the motor 220. For example, as the motor housing 211 and/or cap 212 vibrate, the stabilizing O-ring 255 can absorb the vibrations transmitted through the cap 212. The stabilizing O-ring 255 can support the cap 212 to prevent the cap from deforming or deflecting in response to vibrations. In some implementations, the O-ring 255 can act to dampen the vibrations, which can be significant given the high rotational speeds involved in the exemplary device.

In further embodiments, a damping material can also be applied around the motor 220 to further dampen vibrations. The damping material can be any suitable damping material, e.g., a visco-elastic or elastic polymer. For example, the damping material may be applied between the motor mount 226 and the motor 220 in some embodiments. In addition, the damping material may also be applied around the body of the motor 220 between the motor 220 and the motor housing 211. In some implementations, the damping material may be captured by a rib formed in the motor housing 211. The rib may be formed around the motor 220 in some embodiments.

Turning to FIG. 10C, a proximal end of the driven assembly 201 is shown. As explained above, the flow diverter 205 (or the flow diverter housing in some embodiments) can include an arcuate channel 263 formed in an outer surface of the flow diverter 205. The arcuate channel 263 can be sized and shaped to receive the locking O-ring 253 when the flow diverter 205 is inserted into the opening 202 of the drive assembly 203. As the flow diverter 205 is axially translated through the recess or opening 202, the locking O-ring 253 can be urged or slid over an edge of the channel 263 and can be retained in the arcuate channel 263. Thus, the locking O-ring 253 and the arcuate channel 263 can operate to act as a second securement device. Axial forces applied to the motor assembly 206 can thereby be mechanically resisted, as the walls of the arcuate channel 263 bear against the locking O-ring 253 to prevent the locking o-ring 253 from translating relative to the arcuate channel 263. In various arrangements, other internal locking mechanisms (e.g., within the driven assembly 201 and/or the drive assembly 203) can be provided to secure the driven and drive assemblies 201, 203 together. For example, the driven magnet 204 and the drive magnet 221 may be configured to assist in securing the two assemblies together, in addition to aligning the poles of the magnets. Other internal locking mechanisms may be suitable.

FIG. 10C also illustrates a resealable member 266 disposed within the proximal end portion of the driven assembly 201, e.g., the proximal end of the catheter assembly 100A as shown in FIG. 4. As in FIG. 4, the proximal guidewire opening 237 can be formed in the resealable member 266. As explained above with respect to FIG. 4, the guidewire 235 can be inserted through the proximal guidewire opening 237 and can be maneuvered through the patient's vasculature. After guiding the operative device of the pump to the heart, the guidewire 235 can be removed from the catheter assembly 100A by pulling the guidewire 235 out through the proximal guidewire opening 237. Because fluid may be introduced into the flow diverter 205, it can be advantageous to seal the proximal end of the flow diverter 205 to prevent fluid from leaking out of the catheter assembly 100A. The resealable member 266 can therefore be formed of an elastic, self-sealing material that is capable of closing and sealing the proximal guidewire opening 237 when the guidewire 235 is removed. The resealable member can be formed of any suitable material, such as an elastomeric material. In some implementations, the resealable member 266 can be formed of any suitable polymer, e.g., a silicone or polyisoprene polymer. Skilled artisans will understand that other suitable materials may be used.

FIG. 11 illustrates yet another embodiment of a motor assembly 206A coupled to a catheter assembly. In FIG. 11, a flow diverter is disposed over and coupled to a catheter body 271 that can include a multi-lumen sheath configured to transport fluids into and away from the catheter assembly. The flow diverter 205A can provide support to the catheter body 271 and a drive shaft configured to drive the impeller assembly. Further, the motor assembly 206A can include a motor 220A that has a hollow lumen therethrough. Unlike the embodiments disclosed in FIGS. 4-10C, the guidewire 235 may extend through the proximal guidewire opening 237A formed proximal to the motor 220A, rather than between the motor 220A and the flow diverter 205A. A resealable member 266A may be formed in the proximal guidewire opening 237A such that the resealable member 266A can close the opening 237A when the guidewire 235 is removed from the catheter assembly. A rotary seal 273 may be disposed inside a lip of the flow diverter 205A. The rotary seal 273 may be disposed over and may contact a motor shaft extending from the motor 220A. The rotary seal 273 can act to seal fluid within the flow diverter 205A. In some embodiments, a hydrodynamic seal can be created to prevent fluid from breaching the rotary seal 273.

In the implementation of FIG. 11, the motor 220A can be permanently secured to the flow diverter 205A and catheter assembly. Because the proximal guidewire opening 237 is positioned proximal the motor, the motor 220A need not be coupled with the catheter assembly in a separate coupling step. The motor 220A and the catheter assembly can thus be disposable in this embodiment. The motor 220A can include an output shaft and rotor magnetically coupled with a rotatable magnet in the flow diverter 205A. The motor 220A can also include a plurality of windings that are energized to directly drive the rotatable magnet in the flow diverter 205A.

Figure 12B:
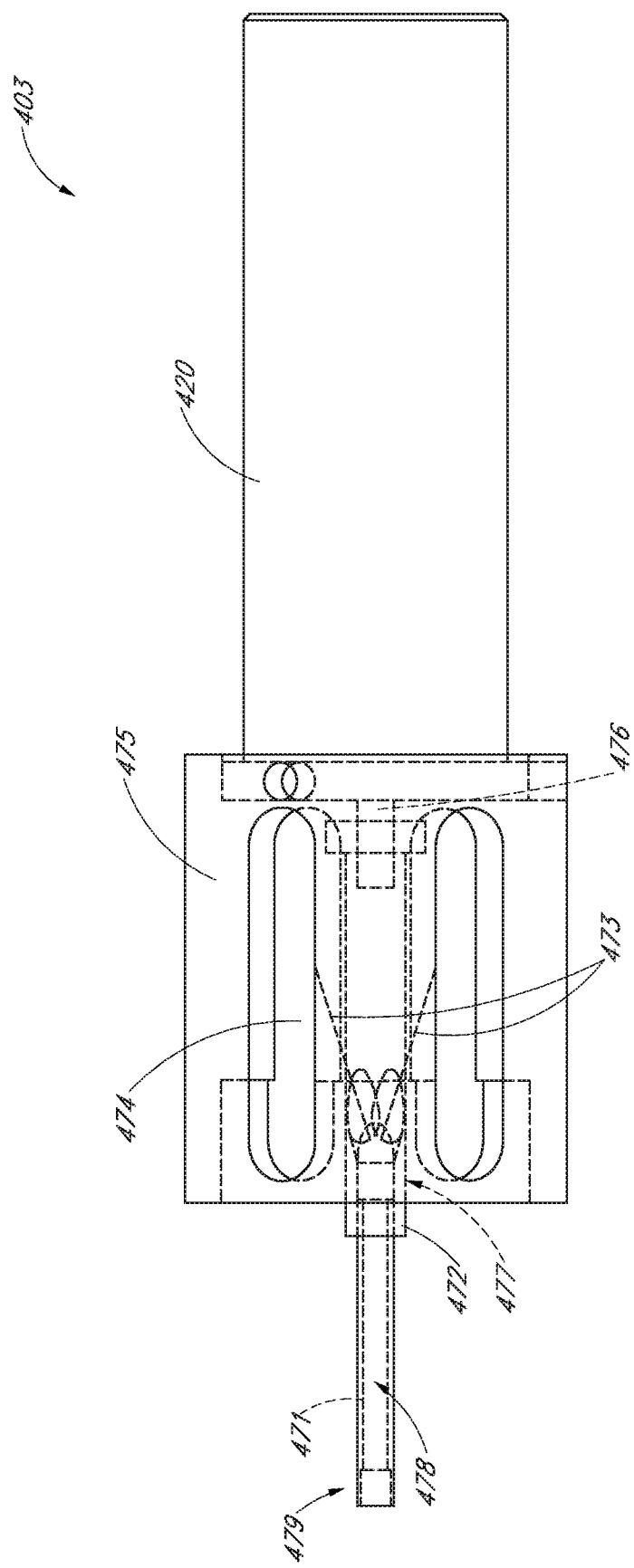

FIGS. 12A-12B illustrate another embodiment of a motor coupling having a driven assembly 401 and a drive assembly 403. Unlike the implementations disclosed in FIGS. 4-10C, however, the embodiment of FIGS. 12A-12B can include a mechanical coupling disposed between an output shaft of a motor and a proximal end of a flexible drive shaft or cable. Unlike the implementations disclosed in FIG. 11, however, the embodiment of FIGS. 12A-12B can include a guidewire guide tube that terminates at a location distal to a motor shaft 476 that extends from a motor 420. As best shown in FIG. 12B, an adapter shaft 472 can operably couple to the motor shaft 476 extending from the motor 420. A distal end portion 477 of the adapter shaft 472 can mechanically couple to a proximal portion of an extension shaft 471 having a central lumen 478 therethrough. As shown in FIG. 12B, one or more trajectories 473 can be formed in channels within a motor housing 475 at an angle to the central lumen 478 of the extension shaft 471. The motor housing 475 can enclose at least the adapter shaft 472 and can include one or more slots 474 formed through a wall of the housing 475.

In some implementations, a guidewire (not shown in FIG. 12B) may pass through the guidewire guide tube from the distal end portion of the catheter assembly and may exit the assembly through the central lumen 478 near the distal end portion 477 of the adapter shaft 472 (or, alternatively, near the proximal end portion of the extension shaft 471). In some embodiments, one of the extension shaft 471 and the adapter shaft 472 may include a resealable member disposed therein to reseal the lumen through which the guidewire passes, as explained above. In some embodiments, the extension shaft 471 and the adapter shaft 472 can be combined into a single structure. When the guidewire exits the central lumen 478, the guidewire can pass along the angled trajectories 473 which can be formed in channels and can further pass through the slots 474 to the outside environs. The trajectories 473 can follow from angled ports in the adapter shaft 472. A clinician can thereby pull the guidewire through the slots 474 such that the end of the guidewire can easily be pulled from the patient after guiding the catheter assembly to the heart chamber or other desired location. Because the guidewire may extend out the side of the housing 475 through the slots, the motor shaft 476 and motor 420 need not include a central lumen for housing the guidewire. Rather, the motor shaft 476 may be solid and the guidewire can simply pass through the slots 474 formed in the side of the housing 475.

Furthermore, the drive assembly 403 can mechanically couple to the driven assembly 401. For example, a distal end portion 479 of the extension shaft 471 may be inserted into an opening in a flow diverter housing 455. The distal end portion 479 of the extension shaft 471 may be positioned within a recess 451 and may couple to a proximal end of a drive cable 450 that is mechanically coupled to the impeller assembly. A rotary seal 461 may be positioned around the opening and can be configured to seal the motor 420 and/or motor housing 475 from fluid within the flow diverter 405. Advantageously, the embodiments of FIGS. 12A-B allow the motor 420 to be positioned proximal of the rotary seal in order to minimize or prevent exposing the motor 420 to fluid that may inadvertently leak from the flow diverter. It should be appreciated that the extension shaft 471 may be lengthened in order to further isolate or separate the motor 420 from the fluid diverter 405 in order to minimize the risk of leaking fluids.

Figure 13:
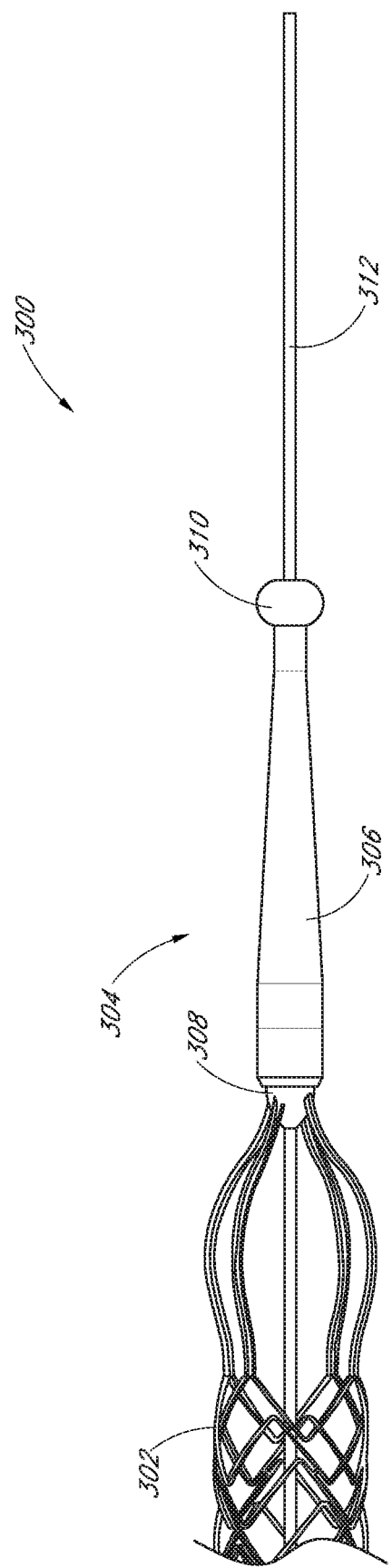
FIG. 13 is a side view of a distal tip member disposed at a distal end of the catheter assembly, according to one embodiment.

Turning to FIG. 13, further features that may be included in various embodiments are disclosed. FIG. 13 illustrates a distal end portion 300 of a catheter assembly, such as the catheter assembly 100A described above. As shown a cannula housing 302 can couple to a distal tip member 304. The distal tip member 304 can be configured to assist in guiding the operative device of the catheter assembly, e.g., an impeller assembly (which can be similar to or the same as impeller assembly 116A), along the guidewire 235. The exemplary distal tip member 304 is formed of a flexible material and has a rounded end to prevent injury to the surrounding tissue. If the distal tip member 304 contacts a portion of the patient's anatomy (such as a heart wall or an arterial wall), the distal tip member 304 will safely deform or bend without harming the patient. The tip can also serve to space the operative device away from the tissue wall. In addition, a guidewire guide tube 312, discussed above with reference to FIG. 4, can extend through a central lumen of the catheter assembly. Thus, the guidewire guide tube 312 can pass through the impeller shaft (not shown, as the impeller is located proximal to the distal end portion 300 shown in FIG. 13) and a lumen formed within the distal tip member 304. In the embodiment of FIG. 13, the guidewire guide tube 312 may extend distally past the distal end of the distal tip member 304. As explained above, in various embodiments, the clinician can introduce a proximal end of the guidewire into the distal end of the guidewire guide tube 312, which in FIG. 13 extends distally beyond the tip member 304. Once the guidewire 235 has been inserted into the patient, the guidewire guide tube 312 can be removed from the catheter assembly in some implementations.

The distal tip member 304 can comprise a flexible, central body 306, a proximal coupling member 308, and a rounded tip 310 at the distal end of the tip member 304. The central body 306 can provide structural support for the distal tip member 304. The proximal coupling member 308 can be coupled to or integrally formed with the central body 306. The proximal coupling member 308 can be configured to couple the distal end of the cannula housing 302 to the distal tip member 304. The rounded tip 310, also referred to as a ball tip, can be integrally formed with the central body 306 at a distal end of the tip member 304. Because the rounded tip 310 is flexible and has a round shape, if the tip member 304 contacts or interacts with the patient's anatomy, the rounded tip 310 can have sufficient compliance so as to deflect away from the anatomy instead of puncturing or otherwise injuring the anatomy. As compared with other potential implementations, the distal tip member 304 can advantageously include sufficient structure by way of the central body 306 such that the tip member 304 can accurately track the guidewire 235 to position the impeller assembly within the heart. Yet, because the tip member 304 is made of a flexible material and includes the rounded tip 310, any mechanical interactions with the anatomy can be clinically safe for the patient.

One potential problem with the embodiment of FIG. 13 is that it can be difficult for the clinician to insert the guidewire into the narrow lumen of the guidewire guide tube 312. Since the guidewire guide tube 312 has a small inner diameter relative to the size of the clinician's hands, the clinician may have trouble inserting the guidewire into the distal end of the guidewire guide tube 312, which extends past the distal end of the tip member 304 in FIG. 13. In addition, when the clinician inserts the guidewire into the guidewire guide tube 312, the distal edges of the guidewire guide tube 312 may scratch or partially remove a protective coating applied on the exterior surface of the guidewire. Damage to the coating on the guidewire may harm the patient as the partially uncoated guidewire is passed through the patient's vasculature. Accordingly, it can be desirable in various arrangements to make it easier for the clinician to insert the guidewire into the distal end of the catheter assembly, and/or to permit insertion of the guidewire into the catheter assembly while maintaining the protective coating on the guidewire.

Additionally, as explained herein, the cannula housing 302 (which may form part of an operative device) may be collapsed into a stored configuration in some embodiments such that the cannula housing is disposed within an outer sheath. When the cannula housing 302 is disposed within the outer sheath, a distal end or edge of the outer sheath may abut the tip member 304. In some cases, the distal edge of the outer sheath may extend over the tip member 304A, or the sheath may have an outer diameter such that the distal edge of the outer sheath is exposed. When the sheath is advanced through the patient's vasculature, the distal edge of the outer sheath may scratch, scrape, or otherwise harm the anatomy. There is a therefore a need to prevent harm to the patient's anatomy due to scraping of the distal edge of the sheath against the vasculature.

Figure 14:
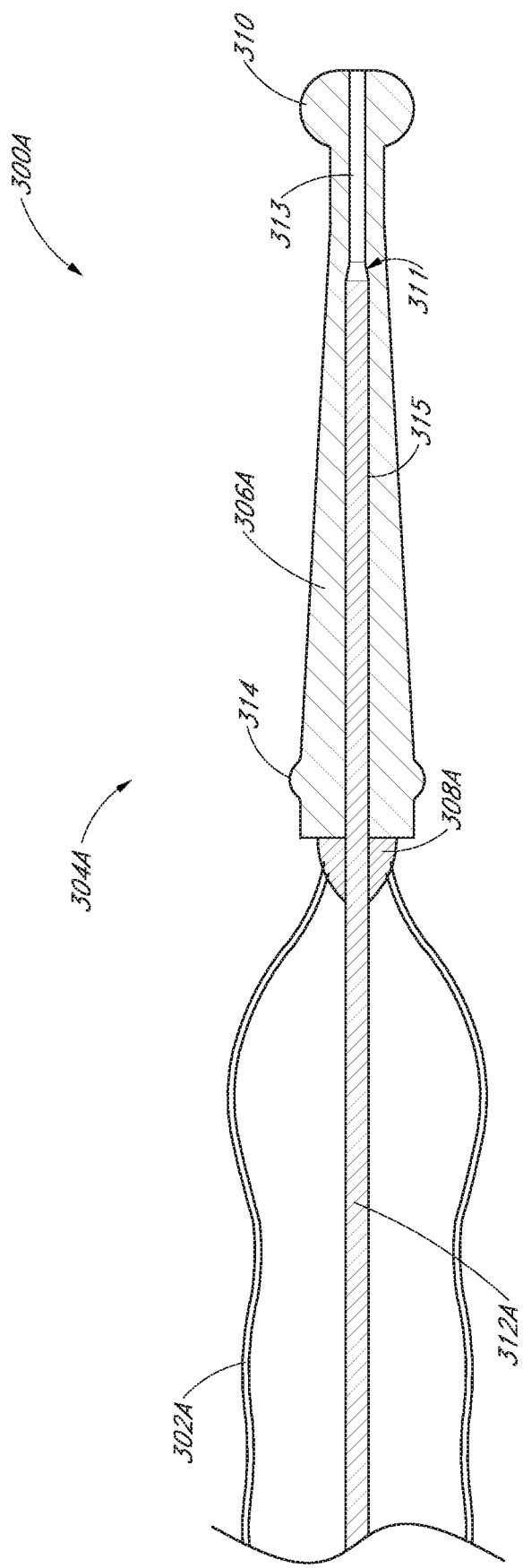
FIG. 14 is a side cross-sectional view of a distal tip member disposed at a distal end of the catheter assembly, according to another embodiment.

FIG. 14 is a side cross-sectional view of a distal tip member 304A disposed at a distal end 300A of the catheter assembly, according to another embodiment. Unless otherwise noted, the reference numerals in FIG. 14 may refer to components similar to or the same as those in FIG. 13. For example, as with FIG. 13, the distal tip member 304A can couple to a cannula housing 302A. The distal tip member 304A can include a flexible, central body 306A, a proximal coupling member 308A, and a rounded tip 310A at the distal end of the tip member 304A. Furthermore, as with FIG. 13, a guidewire guide tube 312A can pass through the cannula housing 302A and a lumen passing through the distal tip member 304A.

However, unlike the embodiment of FIG. 13, the central body 306A can include a bump 314 disposed near a proximal portion of the tip member 304A. The bump 314 illustrated in FIG. 14 may advantageously prevent the outer sheath from scraping or scratching the anatomy when the sheath is advanced through the patient's vascular system. For example, when the cannula housing 302A is disposed within the outer sheath, the sheath will advance over the cannula housing 302A such that the distal edge or end of the sheath will abut or be adjacent the bump 314 of the tip member 304A. The bump 314 can act to shield the patient's anatomy from sharp edges of the outer sheath as the distal end 300A is advanced through the patient. Further, the patient may not be harmed when the bump 314 interact with the anatomy, because the bump 314 includes a rounded, smooth profile. Accordingly, the bump 314 in FIG. 14 may advantageously improve patient outcomes by further protecting the patient's anatomy.

Furthermore, the guidewire guide tube 312A of FIG. 14 does not extend distally past the end of the tip member 306A. Rather, in FIG. 14, the central lumen passing through the tip member 304A may include a proximal lumen 315 and a distal lumen 313. As shown in FIG. 14, the proximal lumen 315 may have an inner diameter larger than an inner diameter of the distal lumen 313. A stepped portion or shoulder 311 may define the transition between the proximal lumen 315 and the distal lumen 313. As illustrated in FIG. 14, the inner diameter of the proximal lumen 315 is sized to accommodate the guidewire guide tube 312A as it passes through a portion of the tip member 304A. However, the inner diameter of the distal lumen 313 in FIG. 14 is sized to be smaller than the outer diameter of the guidewire guide tube 312A such that the guidewire guide tube 312A is too large to pass through the distal lumen 313 of the tip member 304A. In addition, in some embodiments, the thickness of the guidewire guide tube 312A may be made smaller than the height of the stepped portion or shoulder 311, e.g., smaller than the difference between the inner diameter of the proximal lumen 315 and the inner diameter of the distal lumen 313. By housing the guidewire guide tube 312A against the shoulder 311, the shoulder 311 can protect the outer coating of the guidewire when the guidewire is inserted proximally from the distal lumen 313 to the proximal lumen 315.

The embodiment illustrated in FIG. 14 may assist the clinician in inserting the guidewire (e.g., the guidewire 235 described above) into the distal end 300A of the catheter assembly. For example, in FIG. 14, the guidewire guide tube 312A may be inserted through the central lumen of the catheter assembly. For example, the guidewire guide tube 312A may pass distally through a portion of the motor, the catheter body, the impeller assembly and cannula housing 302A, and through the proximal lumen 315 of the tip member 304A. The guidewire guide tube 312A may be urged further distally until the distal end of the guidewire guide tube 312A reaches the shoulder 311. When the distal end of the guidewire guide tube 312A reaches the shoulder 311, the shoulder 311 may prevent further insertion of the guidewire guide tube 312 in the distal direction. Because the inner diameter of the distal lumen 313 is smaller than the outer diameter of the guidewire guide tube 312A, the distal end of the guidewire guide tube 312A may be disposed just proximal of the shoulder 311, as shown in FIG. 14.

The clinician may insert the proximal end of the guidewire (such as the guidewire 235 described above) proximally through the distal lumen 313 passing through the rounded tip 310A at the distal end of the tip member 304A. Because the tip member 304A is flexible, the clinician can easily bend or otherwise manipulate the distal end of the tip member 304A to accommodate the small guidewire. Unlike the guidewire guide tube 312A, which may be generally stiffer than the tip member 304A, the clinician may easily deform the tip member 304A to urge the guidewire into the distal lumen 313. Once the guidewire is inserted in the distal lumen 313, the clinician can urge the guidewire proximally past the stepped portion 311 and into the larger guidewire guide tube 312A, which may be positioned within the proximal lumen 315. Furthermore, since most commercial guidewires include a coating (e.g. a hydrophilic or antomicrobial coating, or PTFE coating), the exemplary guide tube and shoulder advantageously avoid damaging or removing the coating. When the wall thickness of the guidewire guide tube 312A is less than the height of the step or shoulder 311, the shoulder 311 may substantially prevent the guidewire guide tube 312A from scraping the exterior coating off of the guidewire. Instead, the guidewire easily passes from the distal lumen 313 to the proximal lumen 315. The guidewire may then be urged proximally through the impeller and catheter assembly until the guidewire protrudes from the proximal end of the system, such as through the proximal guidewire opening 237 described above with reference to FIG. 4.

Although the inventions herein have been described with reference to particular embodiments, it is to be understood that these embodiments are merely illustrative of the principles and applications of the present inventions. It is therefore to be understood that numerous modifications can be made to the illustrative embodiments and that other arrangements can be devised without departing from the spirit and scope of the present inventions as defined by the appended claims. Thus, it is intended that the present application cover the modifications and variations of these embodiments and their equivalents.

What is claimed is:

1. A motor assembly for a pump extending at a distal end of a catheter, the motor assembly comprising:
   an electric motor extending from a proximal end of the catheter opposite the pump, the electric motor comprising:
   a rotor configured to rotate about a longitudinal axis of the catheter;
   a first shaft mechanically coupled to and extending longitudinally away from the rotor toward the proximal end of the catheter;
   an adapter shaft operably coupled to the first shaft and extending between the first shaft and the proximal end of the catheter;
   a second shaft mechanically coupled to the adapter shaft opposite the first shaft; and
   a guidewire guide tube extending longitudinally through the second shaft and terminating at the adapter shaft distal of the first shaft;
   wherein the adapter shaft is configured to enable a guidewire to extend at least partially radially from the adapter shaft and guidewire guide tube.

2. The motor assembly of claim 1, wherein the adapter shaft includes at least one slot through which the guidewire extends.

3. The motor assembly of claim 1, wherein the adapter shaft comprises a resealable member positioned in a lumen through which the guidewire extends, the resealable member configured to enable the guidewire to pass through and form a fluid seal upon removal of the guidewire.

4. The motor assembly of claim 1, wherein the second shaft comprises a resealable member positioned in a lumen through which the guidewire extends, the resealable member configured to enable the guidewire to pass through and form a fluid seal upon removal of the guidewire.

5. The motor assembly of claim 1, further comprising a motor housing in which the first shaft and at least a portion of the adapter shaft are disposed, the motor housing comprising at least one slot through which the guidewire extends.

6. The motor assembly of claim 1, wherein the adapter shaft and the second shaft are formed from a single structural body.

7. The motor assembly of claim 1, wherein the first shaft comprises a solid shaft having no lumen extending therethrough.

8. The motor assembly of claim 1, wherein the second shaft is configured to be inserted into a recess of a driven assembly.

9. The motor assembly of claim 8, wherein the driven assembly comprises a rotary seal positioned at an opening of the recess and configured to form a seal within the driven assembly to prevent fluid from escaping.

10. A catheter pump assembly, comprising:
    an elongate catheter body through which a drive shaft extends between a proximal end and a distal end of the catheter;
    a pump assembly coupled to the distal end of the elongate catheter body and operably coupled to the drive shaft; and
    a motor assembly extending from a proximal end of the elongate catheter body, the motor assembly comprising:
    an electric motor comprising a rotor configured to rotate about a longitudinal axis of the elongate catheter body;
    a first shaft mechanically coupled to the rotor and extending toward the proximal end of the elongate catheter body;
    an adapter shaft operably coupled to the first shaft and extending between the first shaft and the proximal end of the elongate catheter body;
    a second shaft mechanically coupled to a distal adapter shaft end opposite the first shaft; and
    a guidewire guide tube extending distally through the elongate catheter body and proximally through the second shaft and terminating at the adapter shaft distal of the first shaft;
    wherein the adapter shaft is configured to enable a guidewire to extend at least partially radially from the adapter shaft and guidewire guide tube.

11. The catheter pump assembly of claim 10, wherein the second shaft is mechanically coupled to the drive shaft extending through the elongate catheter body.

12. The catheter pump assembly of claim 10, wherein the second shaft is electromagnetically coupled to the drive shaft extending through the elongate catheter body.

13. The catheter pump assembly of claim 10, wherein the adapter shaft includes at least one slot through which the guidewire extends.

14. The catheter pump assembly of claim 10, wherein the adapter shaft comprises a resealable member positioned in a lumen through which the guidewire extends, the resealable member configured to enable the guidewire to pass through and form a fluid seal upon removal of the guidewire.

15. The catheter pump assembly of claim 10, wherein the second shaft comprises a resealable member positioned in a lumen through which the guidewire extends, the resealable member configured to enable the guidewire to pass through and form a fluid seal upon removal of the guidewire.

16. The catheter pump assembly of claim 10, further comprising a motor housing in which the first shaft and at least a portion of the adapter shaft are disposed, the motor housing including at least one slot through which the guidewire extends.

17. The catheter pump assembly of claim 10, wherein the adapter shaft and the second shaft are formed from a single structural body.

18. The catheter pump assembly of claim 10, wherein the first shaft is a solid shaft having no lumen extending therethrough.

19. The catheter pump assembly of claim 10, wherein the second shaft is configured to be inserted into a recess of a driven assembly coupled to a proximal end of the elongate catheter body.

20. The catheter pump assembly of claim 19, wherein the driven assembly comprises a rotary seal positioned at an opening of the recess and configured to form a seal within the driven assembly to prevent fluid from escaping.

\* \* \* \* \*